United States Patent
Wagle et al.

(10) Patent No.: US 6,610,716 B2
(45) Date of Patent: Aug. 26, 2003

(54) CYANOMETHYL SUBSTITUTED THIAZOLIUMS AND IMIDAZOLIUMS AND TREATMENTS OF DISORDERS ASSOCIATED WITH PROTEIN AGING

(75) Inventors: Dilip R. Wagle, New York, NY (US); Sheng Ding Fang, Mount Kisco, NY (US)

(73) Assignee: Alteon Incorporated, Ramsey, NJ (US)

(*) Notice: Subject to any disclaimer, the term of this patent is extended or adjusted under 35 U.S.C. 154(b) by 0 days.

(21) Appl. No.: 09/905,035

(22) Filed: Jul. 13, 2001

(65) Prior Publication Data

US 2002/0103182 A1 Aug. 1, 2002

Related U.S. Application Data

(60) Provisional application No. 60/218,273, filed on Jul. 13, 2000.

(51) Int. Cl.⁷ .................. A61K 31/4164; A61K 31/426; C07D 233/64; C07D 277/22; C07D 277/24
(52) U.S. Cl. ............... 514/365; 514/367; 514/394; 514/399; 548/152; 548/202; 548/205; 548/309.7; 548/336.1
(58) Field of Search .................... 548/309.7, 152, 548/202, 205, 336.1; 514/367, 365, 394, 399

(56) References Cited

U.S. PATENT DOCUMENTS 5,853,703 A    12/1998   Cerami et al. ................ 424/53

OTHER PUBLICATIONS

Littman et al., Mycopathol. Mycol. Appl. 21(3–4), pp. 289–314, 1963.*

Yount et al., J. Biol. Chem., vol. 34, 1959, pp. 738–741.*

Washabaugh, et al., Biochemistry (1988), 27(14), pp. 5044–5053.*

Littman et al., CA 61:7408b, (1964).*

Washabaugh et al., Thiazolium C(2)–Proton Exchange: General–Base Catalysis, Direct Proton Transfer, and Acid Inhibition, J. Am. Chem. Soc., pp. 674683 (1998).

Washabaugh. et al., Hydrolysis of Thiamin: Evidence for Rate–Limiting Breakdown of the Tricyclic Dihydrothiachromine Intermediate in Neutral Aqueous Solution, Bioorg. Chem., (21)170–191 (1993).

* cited by examiner

Primary Examiner—Laura L. Stockton
(74) Attorney, Agent, or Firm—Mintz Levin; Ivor R. Elrifi; Matthew J. Golden

(57) ABSTRACT

Provided, among other things, is a compound of the formula:

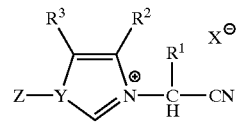

23 Claims, No Drawings

CYANOMETHYL SUBSTITUTED THIAZOLIUMS AND IMIDAZOLIUMS AND TREATMENTS OF DISORDERS ASSOCIATED WITH PROTEIN AGING

This application claims the priority of Serial No. 60/218,273, filed Jul. 13, 2000.

The present invention relates, among other things, to thiazolium and imidazolium compounds and, in an animal, (i) improving the elasticity or reducing wrinkles of a skin, treating (ii) diabetes or treating, inhibiting the (iii) discoloration of teeth, or ameliorating one or more of the following conditions: (iv) adverse sequelae of diabetes, (v) kidney damage, (vi) damage to blood vasculature, (vii) hypertension, (viii) retinopathy, (ix) damage to lens proteins, (x) cataracts, (xi) peripheral neuropathy, (xii) osteoarthritis, or (xiii) damage to cardiovascular tissue due to heart failure, (xiv) improving myocardial elasticity, (xv) preventing damage to tissues in the intraperitoneal cavity caused by contact with elevated levels of reducing sugars, or (xvi) treating or ameliorating other indications described herein.

The reaction between glucose and proteins has been known for some time. Maillard in 1912, observed that glucose or other reducing sugars react with amino acids to form adducts that undergo a series of dehydrations and rearrangements to form stable brown pigments. Further studies have suggested that stored and heat treated foods undergo nonenzymatic browning as a result of the reaction between glucose and polypeptides, resulting in cross-links and decreased bioavailability.

This reaction between reducing sugars and food proteins was found to have its parallel in vivo. Nonenzymatic reaction between glucose and the free amino groups on proteins to form a stable, 1-deoxyketosyl adduct, known as the Amadori product, has been shown to occur with hemoglobin, where a reaction of the amino terminal of the beta-chain of hemoglobin with glucose forms the adduct known as hemoglobin Alc. Like reactions have been found to occur with a variety of other body proteins, such as lens crystallins, collagen and nerve proteins. See Bucala et al., "Advanced Glycosylation; Chemistry, Biology, and Implications for Diabetes and Aging" in Advances in Pharmacology, Vol. 23, pp. 1–34, Academic Press (1992).

Brown pigments with spectral and fluorescent properties similar to those of late-stage Maillard products have also been observed in vivo in association with several long-lived proteins, such as lens proteins and collagen from aged individuals. An age-related linear increase in pigment has been observed in human dura collagen between the ages of 20 to 90 years. Interestingly, the aging of collagen can be mimicked in vitro by cross-linking induced by glucose. Glucose-induced collagen products react with and capture other proteins, which capture is theorized to occur by a crosslinking reaction. This type of reaction is believed to account for the observed accumulation of albumin and antibodies in kidney basement membrane. These reaction products with glucose are typically referred to as "advanced glycosylation endproducts" or AGEs.

Reagents have been identified that inhibit the formation of advanced glycosylation endproducts. These are believed to operate by reacting with an early glycosylation product. Some such reagents are believed to operate by breaking at least certain sugar-derived crosslinks. One of the agents identified as an inhibitor was aminoguanidine, and further testing has borne out its efficacy.

While the success that has been achieved with aminoguanidine and other compounds is promising, a need continues to exist to identify and develop additional inhibitors that broaden the availability and perhaps the scope of this potential activity and its diagnostic and therapeutic utility.

Now, as part of studies on AGE inhibiting or reversing compounds, it has been identified that these compounds inhibit the formation of bioactive agents, such as growth factors and inflammatory mediators, that are associated with a number of indications. These agents include vascular endothelial growth factor (VEGF) and TGF [beta]. As a result, a number of new indications have been identified for treatment with agents that inhibit the formation of, or more preferably break, AGE-mediated cross-links. It is not unreasonable to infer that the effects seen are due to the removal of AGE-related molecules that provide a stimulus for the production or release of these growth factors. Removal of such molecules is believed to proceed in part due to the elimination of AGE-related cross-links that lock the AGE-modified proteins in place. Moreover, such compounds also reduce the expression of collagen in conditions associated with excess collagen production. Regardless of the mechanism, now provided are new methods of treating a number of indications.

SUMMARY OF THE INVENTION

The invention relates, among other things, to a compound of the formula:

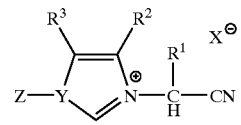

wherein:

Y is N or S;

Z is absent when Y is S and, if present, Z is an alkyl group of 1 to 7 carbon atoms (or of 1 to 6 carbon atoms), vinyl, allyl, arylcarbonyl, amino or alkoxycarbonylalkyl, or Z is according to the formula —CH($R^4$)(CN), or Z is —CH$_2$C(=O)$R^5$, where $R^5$ is (a) a $C_6$–$C_{10}$ aryl group, said aryl group optionally substituted by one or more alkyl, alkoxy, halo, dialkylamino, hydroxy, nitro or $C_1$–$C_2$ alkylenedioxy groups or (b) heterocyclic group containing 4–10 ring members and 1–3 heteroatoms selected from the group consisting of oxygen, nitrogen and sulfur wherein the heterocyclic group can be substituted by one or more substituents selected from the group consisting of alkyl, oxo, alkoxycarbonylalkyl, aryl, and aralkyl group, and the one or more substituents can be substituted by one or more alkyl or alkoxy groups;

$R^1$ and $R^4$ are independently hydrogen, alkyl or phenyl optionally substituted with one or more halogen, alkyl, di(lower alkyl)amino or alkoxy groups when Y is N;

$R^2$ and $R^3$ are:

1. independently selected from hydrogen, acylamino, acyloxyalkyl, alkanoyl, alkanoylalkyl, alkenyl, alkoxy, alkoxycarbonyl, alkoxycarbonylalkyl, alkyl, alkylamino, ($C_1$–$C_3$)alkylenedioxy, allyl, amino, ω-alkylenesulfonic acid, carbamoyl, carboxy, carboxyalkyl, cycloalkyl, dialkylamino, halo, hydroxy, ($C_2$–$C_6$)hydroxyalkyl, mercapto, nitro, sulfamoyl, sulfonic acid, alkylsulfonyl, alkylsulfinyl, alkylthio, trifluoromethyl, azetidin-1-yl, morpholin-4-yl, thiomorpholin-4-yl, piperidin-1-yl, 4-[$C_6$ or $C_{10}$]arylpiperidin-1-yl, 4-[$C_6$ or $C_{10}$]arylpiperazin-1-yl, Ar {wherein, consistent with the rules of aromaticity, Ar is $C_6$ or $C_{10}$ aryl or a 5- or 6-membered heteroaryl ring, wherein 6-membered heteroaryl ring contains one to three atoms of N, and the 5-membered heteroaryl ring contains from one to three atoms of N or one atom of O or S and zero to two atoms of N, each heteroaryl ring can be fused to a benzene, pyridine, pyrimidine, pyridazine, pyrazine, or (1,2,3)triazine (wherein the ring fusion is at a carbon-carbon double bond of Ar)}, Ar-alkyl, Ar—O, ArSO$_2$—, ArSO—, ArS—, ArSO$_2$NH—, ArNH, (N—Ar)(N-alkyl)N—, ArC(O)—, ArC(O)NH—, ArNH—C(O)—, and (N—Ar)(N-alkyl)N—C(O)—, or together $R_1$ and $R_2$ comprise methylenedioxy [in one embodiment, independently selected from hydrogen, acylamino, acyloxyalkyl, alkanoyl, alkanoylalkyl, alkenyl, alkoxy, alkoxycarbonyl, alkoxycarbonylalkyl, alkyl, ($C_1$–$C_3$) alkylenedioxy, allyl, ω-alkylenesulfonic acid, carbamoyl, carboxy, carboxyalkyl, cycloalkyl, halo, hydroxy, ($C_2$–$C_6$)hydroxyalkyl, mercapto, nitro, sulfamoyl, sulfonic acid, alkylsulfonyl, alkylsulfinyl, alkylthio, trifluoromethyl, Ar {wherein, consistent with the rules of aromaticity, Ar is $C_6$ or $C_{10}$ aryl or a 5- or 6-membered heteroaryl ring, wherein 6-membered heteroaryl ring contains one to three atoms of N, and the 5-membered heteroaryl ring contains from one to three atoms of N or one atom of O or S and zero to two atoms of N, each heteroaryl ring can be fused to a benzene, pyrimidine, pyridazine, pyrazine, or (1,2,3)triazine (wherein the ring fusion is at a carbon—carbon double bond of Ar)}, Ar-alkyl, Ar—O, ArSO$_2$—, ArSO—, ArS—, ArSO$_2$NH—, ArNH, (N—Ar)(N-alkyl)N—, ArC(O)—, ArC(O)NH—, ArNH—C(O)—, and (N—Ar)(N-alkyl)N—C(O)—]; or 2. together with their ring carbons form a $C_6$- or $C_{10}$- aromatic fused ring system; or
3. together with their ring carbons form a $C_5$–$C_7$ fused cycloalkyl ring having up to two double bonds including the fused double bond of the -olium or -onium containing ring, which cycloalkyl ring can be substituted by one or more of the group consisting of alkyl, alkoxycarbonyl, amino, aminocarbonyl, carboxy, fluoro, or oxo substituents [in one embodiment, together with their ring carbons form a $C_5$–$C_7$ fused cycloalkyl ring having up to two double bonds including the fused double bond of the -olium or -onium containing ring, which cycloalkyl ring can be substituted by one or more of the group consisting of alkyl, alkoxycarbonyl, aminocarbonyl, carboxy, fluoro, or oxo substituents]; or
4. together with their ring carbons form a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each heteroaryl ring may be optionally substituted with one or more 1-pyrrolidinyl-, 4-[$C_6$ or $C_{10}$]arylpiperazin-1-yl, 4-[$C_6$ or C1o]arylpiperidin-1-yl, azetidin-1-yl, morpholin-4-yl, thiomorpholin-4-yl, piperidin-1-yl, halo or ($C_1$–$C_3$)alkylenedioxy groups [in one embodiment, together with their ring carbons form a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each heteroaryl ring may be optionally substituted with one or more halo or ($C_1$–$C_3$)alkylenedioxy groups]; or
5. together with their ring carbons form a five to eight membered heterocycle, wherein the heterocycle consists of ring atoms selected from the group consisting of carbon, nitrogen, and $S(O)_n$, where n=0, 1, or 2;

and in one preferred embodiment $R^2$ and $R^3$ are independently hydrogen, alkyl, or together form an alkylene bridge of 3–4 carbon atoms; and $X^-$ is a biologically or pharmaceutically acceptable anion.

Optionally, aryl or Ar can be substituted with, in addition to any substitutions specifically noted, one or more substituents selected from the group consisting of acylamino, acyloxyalkyl, alkanoyl, alkanoylalkyl, alkenyl, alkoxy, alkoxycarbonyl, alkoxycarbonylalkyl, alkyl, alkylamino, (C1–C3)alkylenedioxy, alkylsulfonyl, alkylsulfinyl, co-alkylenesulfonic acid, alkylthio, allyl, amino, ArC(O)—, ArC(O)NH—, ArO—, Ar—, Ar-alkyl-, carboxy, carboxyalkyl, cycloalkyl, dialkylamino, halo, trifluoromethyl, hydroxy, (C2–C6)hydroxyalkyl, mercapto, nitro, sulfamoyl, sulfonic acid, 1-pyrrolidinyl, 4-[C6 or C10]arylpiperazin-1-yl-, 4-[C6 or C1O]arylpiperidin-1-yl, azetidin-1-yl, morpholin-4-yl, thiomorpholin-4-yl, piperidin-1-yl; and heterocycles, except those of Ar, can be substituted with, in addition to any substitutions specifically noted, acylamino, alkanoyl, alkoxy, alkoxycarbonyl, alkoxycarbonylalkyl, alkyl, alkylamino, alkylsulfonyl, alkylsulfinyl, alkylthio, amino, ArC(O)—, ArO—, Ar—, carboxy, dialkylamino, fluoro, fluoroalkyl, difluoroalkyl, hydroxy, mercapto, sulfamoyl, or trifluoromethyl [in one embodiment, aryl or Ar can be substituted with, in addition to any substitutions specifically noted, one or more substituents selected from the group consisting of acylamino, acyloxyalkyl, alkanoyl, alkanoylalkyl, alkenyl, alkoxy, alkoxycarbonyl, alkoxycarbonylalkyl, alkyl, ($C_1$–$C_3$) alkylenedioxy, alkylsulfonyl, alkylsulfinyl, co-alkylenesulfonic acid, alkylthio, allyl, ArC(O)—, ArC(O) NH—, ArO—, Ar—, Ar-alkyl-, carboxy, carboxyalkyl, cycloalkyl, halo, trifluoromethyl, hydroxy, ($C_2$–$C_6$) hydroxyalkyl, mercapto, nitro, sulfamoyl, sulfonic acid].

In one embodiment, $R^1$ is hydrogen. In another Z is an alkyl group of 1 to 7 carbon atoms; or Z is $C_1$ to $C_3$ alkyl. In another, R is hydrogen. In one embodiment, Z is an alkyl group of 1 to 7 carbon atoms, arylcarbonyl, amino or alkoxycarbonylalkyl, or Z is according to the formula —CH($R^4$)(CN), or Z is —CH$_2$C(═O)$R^5$, where $R^5$ is a $C_6$–$C_{10}$ aryl group, said aryl group optionally substituted by one or more alkyl, alkoxy, halo, dialkylamino, hydroxy, nitro or $C_1$–$C_2$ alkylenedioxy groups, or Z is an alkyl group of 1 to 7 carbon atoms, arylcarbonyl, amino or alkoxycarbonylalkyl, or Z is according to the formula —CH($R^4$)(CN) [in one embodiment, heterocycles, except those of Ar, can be substituted with, in addition to any substitutions specifically noted, acylamino, alkanoyl, alkoxy, alkoxycarbonyl, alkoxycarbonylalkyl, alkyl, alkylsulfonyl, alkylsulfinyl, alkylthio, ArC(O)—, ArO—, Ar—, carboxy, fluoro, fluoroalkyl, difluoroalkyl, hydroxy, mercapto, sulfamoyl, or trifluoromethyl].

DETAILED DESCRIPTION

Provided, among other things, is a method of, in an animal, (i) improving the elasticity or reducing wrinkles of a skin, treating (ii) diabetes or treating, inhibiting the (iii) discoloration of teeth, or ameliorating one or more of the following conditions: (iv) adverse sequelae of diabetes, (v) kidney damage, (vi) damage to blood vasculature, (vii) hypertension, (viii) retinopathy, (ix) damage to lens proteins, (x) cataracts, (xi) peripheral neuropathy, (xii) osteoarthritis, (xiii) improving myocardial elasticity, or (xiv) ameliorating damage to tissues in the intraperitoneal cavity caused by contact with elevated levels of reducing sugars, the method comprising administering an effective amount of one or more compounds of the formula I. The compounds can further be used to treat or ameliorate one of the indications described below.

Certain Fibrotic Diseases

Among the indications that can be treated with the invention are a number of indications linked to or associated with the formation of excess collagen. Among these, a number of the indications can be termed fibrotic diseases.

Such fibrotic diseases include systemic sclerosis, mixed connective tissue disease, fibrodysplasia, fibrocystic disease, sarcoidosis, myositis (e.g. polymyositis, primary idiopathic polymyositis, childhood polymyositis, dermatomyositis, childhood dennatomyositis, primary idiopathic dermatomyositis in adults, inclusion body myositis, polymyositis or dermatomyositis associated with malignant tumors). Dermatomyositis can be associated with fibrosing or hypertrophic aspects, including fibrosing alveolitis and pulmonary fibrosis. Treatment using the invention is expected to treat, prevent, reduce or ameliorate such diseases or hypertrophy, fibrotic hypertrophy or fibrosis in such diseases. Amelioration includes reducing the rate of progression of a disease.

Among these fibrotic diseases are diseases that have as a manifestation fibrotic vascular intimal hypertrophy. These diseases include vasculitis (including coronary artery vasculitis), polyarteritis nodosa or temporal arteritis. Treatment using the invention is expected to treat, prevent, reduce or ameliorate vascular intimal hypertrophy in such diseases.

These fibrotic diseases further include diseases that have as a manifestation fibrotic hypertrophy of skin and/or muscle tissue. These diseases include scleroderma, eosinophilic fasciitis, discoid lesions associated with lupus or discoid lupus or surgical adhesions. Treatment using the invention is expected to treat, prevent, reduce or ameliorate such indications or hypertrophy or fibrosis of skin or muscle tissue.

Such fibrotic diseases further include diseases that have as a manifestation fibrotic hypertrophy of nerve tissue. These diseases include cerebrosclerosis, annular sclerosis. diffuse sclerosis and lobar sclerosis. Treatment using the invention is expected to treat, prevent, reduce or ameliorate such diseases, or hypertrophy, fibrotic hypertrophy or fibrosis of nerve tissue in such diseases.

These fibrotic diseases further include fibrotic lung diseases that have as a manifestation fibrotic hypertrophy or fibrosis of lung tissue. These diseases include pulmonary fibrosis (or interstitial lung disease or interstitial pulmonary fibrosis), idiopathic pulmonary fibrosis, the fibrotic element of pneumoconiosis (which is associated with exposure to environmental hazards such as smoking, asbestos, cotton lint, stone dust, mine dust and other particles), pulmonary sarcoidosis, fibrosing alveolitis, the fibrotic or hypertrophic element of cystic fibrosis, chronic obstructive pulmonary disease, adult respiratory distress syndrome and emphysema. Treatment using the invention is expected to treat, prevent, reduce or ameliorate such diseases, or hypertrophy, fibrotic hypertrophy or fibrosis in such diseases.

Such fibrotic diseases further include diseases that have as a manifestation fibrotic hypertrophy or fibrosis of prostate, liver, the pleura (e.g., pleurisy, pleural fibrosis) or pancreas. These diseases include benign prostatic hypertrophy (BPH) and fibrosis of the liver. Treatment using the invention is expected to treat, prevent, reduce or ameliorate such diseases, or hypertrophy, fibrotic hypertrophy or fibrosis in such diseases.

These fibrotic diseases further include diseases that have as a manifestation fibrotic hypertrophy or fibrosis of the bowel wall, such as inflammatory bowel disease, including Crohn's disease. Treatment using the invention is expected to treat, prevent, reduce or ameliorate such diseases, or hypertrophy, fibrotic hypertrophy or fibrosis in such diseases.

Arteriosclerosis, Atlerosclerosis, Stiff Vessel Disease, Peripheral Vascular Disease, Coronary Heart Disease, Stroke, Myocardial Infarct, Cardiomyopathies, Restenosis Arteriosclerosis is a disease marked by thickening, hardening, and loss of elasticity in arterial walls, of which atherosclerosis is a sub-type. Arteriosclerosis in turn falls within the genus of stiff vessel diseases. Without limitation to theory, it is believed that damage to the blood vessels of these diseases is due to AGE-caused damage, either through protein cross-liking or the stimulation of bioactive agents, or both. Accordingly, the first agents are used to treat, prevent, reduce or ameliorate stiff vessel disease, including arteriosclerosis and athersclerosis. Peripheral vascular disease is an indication that overlaps with atherosclerosis but also covers disease which is believed to have a stronger inflammatory component. First agents are used to treat, prevent, reduce or ameliorate peripheral vascular disease. Coronary heart disease is a form of atherosclerosis of the coronary arteries. First agents are used to treat, prevent, reduce or ameliorate coronary heart disease.

When the heart pumps blood into the vascular system, the ability of the arteries to expand helps to push blood through the body. When arteries become stiff, as they do in the natural process of aging. the ability of the arteries to expand is diminished and also has consequences for the heart. The heart has to work harder to pump the blood into the stiff arteries, and eventually hypertrophies (enlarges in size) to accomplish this. A hypertrophied heart is an inefficient pump, and is one of the disorders that leads to congestive heart failure. One compound believed to work by a mechanism shared by the compounds of the invention, 3-[2-phenyl-2-oxoethyl]-4,5-dimethyl-thiazolium salt, showed an ability to reverse the stiffness of arteries in a Phase Ia clinical trial, as measured by the ratio of stroke volume (ml) to pulse pressure (mm Hg). The potential clinical benefit of this is to lessen the effort that the heart must expend to push blood throughout the body. The effect is also believed to contribute to preventing hypertrophy and subsequent inefficiency of the heart, which inefficiency would contribute to congestive heart failure.

Stroke is a cardiovascular disease that occurs when blood vessels supplying blood (oxygen and nutrients) to the brain burst or are obstructed by a blood clot or other particle. Nerve cells in the affected area of the brain die within minutes of oxygen deprivation and loss of nerve cell function is followed by loss of corresponding bodily function. Of the four main types of stroke, two are caused by blood clots or other particles. The former two are the most common forms of stroke, accounting for about 70–80 percent of all strokes.

Blood clots usually form in arteries damaged by atherosclerosis. When plaque tears from the sheer forces of blood flowing over an uneven, rigid cap atop the plaque site, thrombotic processes become involved at the "injury" site. As a result, clots can form. First agents are used to prevent, reduce or ameliorate the risk of stroke in patients who have suffered previous strokes or have otherwise been identified as at risk.

First agents can also be used to treat, prevent, reduce or ameliorate peripheral vascular disease and periarticular rigidity.

Treatment with the first agents during the relatively immediate aftermath of a heart attack can be used to reduce the size of the myocardial infarct resulting from the heart attack. This treatment is preferably administered within six hours of the heart attack, more preferably, within three hours. While the dosages discussed below can be used with this indication, such as a dose of 0.01–4.0 mg/kg administered orally or 0.01–2.0 mg/kg administered intravenously, preferably within the time period outlined above. Preferred routes of administration include i.v. injection or i.v. drip. Thereafter, optional supplemental administrations can be made with the dosages described below.

Atherosclerosis is a disease that involves deposition of blood lipids in plaque in the arteries throughout the body. In coronary arteries, accumulation of plaque progressively leads to reduced coronary flow, with occlusion of the arteries causing focal death of cardiac tissue (myocardial infarction, heart attack). If the amount of tissue that dies is large enough, death ensures. In a Phase Ia trial, one compound believed to work by a mechanism shared by the compounds of the invention, 3-[2-phenyl-2-oxoethyl]-4,5-dimethyl-thiazolium salt, increased the amount of circulating triglycerides (lipids). Consistent with the known presence of AGEs in plaque, the result indicates that the agent had a lipid mobilizing effect on arterial plaque. Reducing local deposits of plaque should eventually lessen the risk of myocardial infarction and death due to heart attacks.

Fibrotic diseases further include diseases that have as a manifestation fibrotic hypertrophy of the heart. These diseases include endomyocardial fibrosis (wherein endocardium and subendocardium are fibrosed, such as in some manifestations of restrictive cardiomyopathy), dilated congestive cardiomyopathy (a disorder of myocardial function with heart failure in which ventricular dilation and systolic dysfunction predominate), hypertrophic cardiomyopathy (characterized by marked ventricular hypertrophy with diastolic dysfunction in the absence of an afterload demand), and other cardio-hypertrophies. In dilated congestive cardiomyopathy, typically at presentation there is chronic myocardial fibrosis with diffuse loss of myocytes. In hypertrophic cardiomyopathy, usually the interventricular septum is hypertrophied more than the left ventricular posterior wall (asymmetric septal hypertrophy). Treatment using the invention is expected to treat, prevent, reduce or ameliorate such diseases, or hypertrophy, fibrotic hypertrophy or fibrosis in such diseases.

Hypertrophies of the heart can be diagnosed and monitored by methods known in the art, such as by electrocardiogram, echocardiography or magnetic resonance imaging. Such diagnostic methods can be applied in particular for subjects having a risk factor for such hypertrophy, such as congestive heart failure, prior cardiac surgery or diabetes. In one aspect, the invention comprises identifying cardio-hypertrophy with using biophysical diagnostic tools, and administering an active agent of the invention to treat, prevent, reduce or ameliorate such diseases, or hypertrophy, fibrotic hypertrophy or fibrosis in such diseases. The invention can further include monitoring cardio-hypertrophy during the course of treatment with active agent.

Erosion or tearing of arterial wall plaque can occur due to the rough and irregular shape of the plaque as it forms from deposition of lipids and invasion of cells such as monocytes and macrophages (foam cells). When erosion occurs platelets and other components of the blood clotting system are activated, resulting in formation of a clot (thrombus). When the thrombus grows to such as state that blood flow is reduced, severe angina attacks that characterize unstable angina can occur. Plaque forms irregular shapes and in doing so creates shear stresses from the flow of blood over this irregular form. It is the irregularity of plaque shape that leads to the dislodging or tearing of the plaque, and to the subsequent invasion of reactive cells. On the surface of plaque is collagen, which is believed to contribute to the rigidity of the irregular shape. Without limitation to theory, it is believed that reducing the crosslinking of such a rigid collagen cap results in smoother blood flow, with a reduced risk of angina-causing tears. Accordingly, first agents are used to treat, prevent, reduce or ameliorate unstable angina.

Faithful conduction of the electrical impulse from the sinoatrial to the atrioventricular nodes depends upon close apposition of myocardial cells. Excess production of collagen in the heart, which occurs naturally with aging but more so in diabetes and in conditions of heart disorders such as hypertension, causes an increase in the distance between myocardial cells, leading to atrial fibrillation. First agents are used to treat, prevent, reduce or ameliorate atrial fibrillation.

The fibrotic indications further include restenosis, which is the process of increasing artery closure following an operation to open the artery, such as balloon angioplasty.

Bladder Elasticity

Indications that can be treated, prevented, reduced or ameliorated with the first agents include loss of bladder elasticity. Bladder elasticity is tied to the frequency of urination, and the urgency of desire to urinate. Accordingly, the invention can be used to treat, prevent, reduce or ameliorate non-obstructive uropathy, a disorder characterized by an overactive bladder that entails increased frequency of urination, a strong and sudden desire to urinate (urgency) which may also be associated with involuntary urinary leakage (urge incontinence).

Macular Degeneration

The effect of the first agents in reducing levels of other endogenous bioactive agents, particularly VEGF and/or TGF[beta], is believed to underlie effectiveness against macular degeneration and edema. Again, however, the invention is not limited to theory. Moreover, a anti-fibrotic effect or another effect against tissue hypertrophy may contribute. Treatment using the invention is expected to treat, prevent, reduce or ameliorate macular degeneration or macular edema. In one aspect of the invention, the treatment is used to treat, prevent, reduce or ameliorate the wet form of macular degeneration. In the wet form, new blood vessel growth has a greater contribution to the disease.

Amyotrophic Lateral Sclerosis (ALS)

ALS is associated with degradations of the motor neuron system and/or the posterior column of the spinal cord. In ALS patients, these structures tend to stain with AGE-reactive antibodies. Treatment using the invention is expected to treat, prevent, reduce or ameliorate ALS.

Rheumatoid Arthritis, Osteoarthritis, Bone Resorption

It is believed, without limitation to such theory, that reducing AGE accumulation at the joints affected by rheumatoid arthritis or osteoarthritis reduces stimulation of the production of cytokines involved in inflammatory processes of the disease. Treatment using the invention is expected to treat, prevent, reduce or ameliorate rheumatoid arthritis or osteoarthritis. Similarly, it is believed that reducing AGE accumulation at bone reduces stimulation of bone resorption. Accordingly, the invention is used to treat, prevent, reduce or ameliorate osteoporosis, bone loss or brittle bone.

Dialysis

The first agents can be administered as part of a dialysis exchange fluid, thereby preventing, limiting or ameliorating the damage to tissue caused by the sugars found in such exchange fluid. For example, first agents are expected to prevent, limit or ameliorate the stiffening and sclerosing of peritoneal tissue that occurs in peritoneal dialysis, as well as prevent, limit or ameliorate the formation of new blood vessels in the peritoneal membrane. In hemodialysis, first agents are expected to prevent, limit or ameliorate the stiffening and sclerosing of red blood cells and vasculature resulting from exposure to the sugars exchanged into the blood during dialysis. Exchange fluids for peritoneal dialysis typically contain 10–45 g/L of reducing sugar, typically 25 g/L, which causes the formation of AGEs and consequent stiffening and degradation of peritoneal tissue. Similarly, hemodialysis fluids typically contain up to about 2.7 g/L of reducing sugar, typically 1 to 1.8 g/L. Thus, the invention provides methods by which the first agents are provided in these fluids and thereby prevent, limit or ameliorate the damage that would otherwise result. Alternatively, the invention provides methods whereby the first agents are administered by the methods described below to prevent, limit or ameliorate such damage from dialysis. In hemodialysis, the exchange fluid preferably contains 0.006–2.3 mg/L of an agent of the invention, more preferably, 0.06 to 1.0 mg/L. In peritoneal dialysis, the exchange fluid preferably contains 0.01 to 24 mg/L of an agent of the invention, or preferably, 1.0 to 10 mg/L.

In one embodiment, preventing or ameliorating is effected with a second agent. A preferred route of administration is inclusion in the dialysis fluids. In hemodialysis, the exchange fluid preferably contains 0. 125 to 2.5 mg/L of aminoguanidine, more preferably, 0.2 to 1.0 mg/L. In peritoneal dialysis, the exchange fluid preferably contains 1.25 to 25 mg/L of aminoguanidine, or preferably, 2.0 to 10 mg/L. In a preferred aspect of the invention, the first agents are initially administered, and subsequently second agents are used to moderate or limit damage thereafter.

Asthma

It is believed, without limitation to such theory, that the first agents or second agents act to prevent, reduce or ameliorate the small but significant thickening of the lung airways associated with asthma. Moreover, the agents are believed to reduce stimulation of the production of cytokines involved in inflammatory processes of the disease. Accordingly, the agents are used to treat, prevent, reduce or ameliorate asthma. In this embodiment, one preferred route of administration is pulmonary, such as via an aerosol, though peroral administration is also preferred.

Carpal Tunnel Syndrome

It is believed, without limitation to such theory, that the first agents act to prevent, reduce or ameliorate fibrotic and cytokine-induced elements of carpal tunnel syndrome. Accordingly, the first agents are used to treat, prevent, reduce or ameliorate carpal tunnel syndrome.

Fibrotic diseases also include Dupuytren's contracture, a contracture of the palmar fascia often causing the ring and little fingers to bend into the palm. Treatment using the invention is expected to treat, prevent, reduce or ameliorate Dupuytren's contracture, or hypertrophy, fibrotic hypertrophy or fibrosis in Dupuytren's contracture.

In these embodiments, one preferred route of administration is local injection.

Periodontal Disease

The incidence of periodontal disease is higher in subjects with either insulin-deficient or insulin-resistant diabetes, with consequent hyperglycemia. Again, without limitation to such theory, it is believed that the first agents act to prevent, reduce or ameliorate AGE-induced cytokine action to create or exacerbate periodontal disease. Accordingly, the first or second agents are used to treat, prevent, reduce or ameliorate periodontal disease. In this embodiment, one preferred primary or supplemental route of administration is via mouthwash, or compositions adapted for delivery into the subgingival periodontal pocket (such as implants and erodible microspheres). Peroral administration is again useful. The mouthwash preferably contains 0.003–1.0 mg/L of a first agent, more preferably, 0.01–0.1 mg/L.

Sickle Cell Anemia

It is believed, without limitation to such theory, that the first agents act to prevent, reduce or ameliorate the restraint on blood flow caused by sickling. Again without limitation to theory, the mode of action is believed to be in reducing vascular as well as blood cell inelasticity. Accordingly, the first agents are used to treat, prevent, reduce or ameliorate a sickle cell anemia.

Erectile Dysfunction

Fibrotic diseases further include diseases that have as a manifestation fibrotic disease of the penis, including Peyronie's disease (fibrosis of the cavernous sheaths leading to contracture of the investing fascia of the corpora, resulting in a deviated and painful erection). Treatment using the invention is expected to treat, prevent, reduce or ameliorate such diseases, or hypertrophy, fibrotic hypertrophy or fibrosis in such diseases.

Without limitation to theory, it is believed that the first agents act to prevent, reduce or ameliorate inelasticity of tissue of the penis and/or fibrosis of tissue of the penis, such as inelasticity or fibrosis of the cavernous sheaths leading to contracture of the investing fascia of the corpora. At least partial restoration of the resulting inelasticity is believed to facilitate engorgement of the corpora cavernosa with blood. Accordingly, the first agents are used to treat, prevent, reduce or ameliorate erectile dysfunction.

Limited Joint Mobility

Limited Joint Mobility (LJM) is a disorder associated with diabetes and typically involves the joints of the hands. The fourth and fifth fingers are affected initially by limitation of motion. AGE glycation and crosslinking of tendons (collagen) in the joints is believed to contribute to the disease. It is believed, without limitation to theory, that the first agents act to prevent, reduce or ameliorate inelasticity, fibrous tissue or cytokine-induced inflammation associated with limited joint mobility. Accordingly, the first agents are used to treat, prevent, reduce or ameliorate limited joint mobility.

Antineoplastic Applications

The first agents inhibit the stimulated formation of bioactive agents, such as VEGF, associated with angiogenesis. Angiogenesis is critical for both normal development and the growth and metastasis of solid tumors. Accordingly, the first agents are used to treat, prevent, reduce or ameliorate the growth of neoplasms by limiting the formation of blood vessels needed to sustain the neoplasms.

End Stage Renal Disease, Diabetic Nephropathy

Diabetic Nephropathy is a complication of diabetes that evolves early, typically before clinical diagnosis of diabetes is made. The earliest clinical evidence of nephropathy is the appearance of low but abnormal levels (>30 mg/day or 20 $\mu$g/min) of 30 albumin in the urine (microalbuminuria), followed by albuminuria (>300 mg/24 h or ~200 $\mu$g/min) that develops over a period of 10–15 years. In patients with type 1 diabetes, diabetic hypertension typically becomes manifest early on, by the time that patients develop microalbuminuria. Once overt nephropathy occurs, the glomerular filtration rate (GFR) falls over several years resulting in End Stage Renal Disease (ESRD) in 50% of type 1 diabetic individuals within 10 years and in >75% of type 1 diabetics by 20 years of onset of overt nephropathy. Albuminuria (i.e., proteinuria) is a marker of greatly increased cardiovascular morbidity and mortality for patients with either type 1 or type 2 diabetes.

Without limitation to theory, it is believed that damage to the glomeruli and blood vessels of the kidney is due to AGE-caused damage, either through protein cross-linking or the stimulation of bioactive agents, or both. Accordingly, the first agents are used to treat, prevent, reduce or ameliorate damage to kidney in patients at risk for ESRD. The first agents can also be used to treat, prevent, reduce or ameliorate glomerulosclerosis.

Hypertension, Isolated Systolic Hypertension

Cardiovascular risk correlates more closely with the systolic and the pulse pressure than with the diastolic pressure. In diabetic patients, the cardiovascular risk profile of diabetic patients is strongly correlated to duration of diabetes, glycemic control and blood pressure. Structural matrix proteins contribute to the function of vessels and the heart, and changes in the physical behavior of cardiovascular walls are believed to be important determinants of circulatory function. In elderly individuals, the loss of compliance in the aorta leads to isolated systolic hypertension, which in turn expands the arterial wall and thereby diminishes the dynamic range of elasticity. In vivo studies in rodents, canines and in primates indicate potential utility of 3-[2-phenyl-2-oxoethyl]-4,5-dimethyl-thiazolium salt in substantially ameliorating vascular stiffening. For example, in a dog model for diabetes, lower end diastolic pressure and increased end diastolic volume, indicators of ventricular elasticity, returned to a value at about the mid-point between the disease impaired value and the value for control dogs. Treatment with 3-[2-phenyl-2-oxoethyl]-4,5-dimethyl-thiazolium salt lead to a reduction in the mass of collagen in cardiovascular tissues. In situ hybridization studies demonstrate that 3-[2-phenyl-2-oxoethyl]-4,5-dimethyl-thiazolium salt reduces the expression of both Type IV collagen and TGFbeta.

Compared with that of a non-diabetic, the diabetic artery is smaller as it is stiffer. As in isolated systolic hypertension in which vessels stiffen with age and lose the dynamic range of expansion under systole. First agents are used to treat, prevent, reduce or ameliorate hypertension, including isolated systolic hypertension and diabetic hypertension. Moreover, the same benefit is anticipated for the more rare hypertensive disorder, pulmonary hypertension. Pulmonary hypertension is a rare blood vessel disorder of the lung in which the pressure in the pulmonary artery (the blood vessel that leads from the heart to the lungs) rises above normal levels and may become life threatening. The similarity in development of elevated blood pressure in the pulmonary bed with the increase in systemic blood pressure in diabetic hypertension and in isolated systolic hypertension suggests similar mechanisms are involved.

Pulse pressure is the difference between systolic and diastolic blood pressure. In a young human, systolic pressure is typically 120 mm Hg and diastolic pressure is 80 mm Hg, resulting in a pulse pressure of 40 mm Hg. With age, in many individuals pulse pressure increases, largely due to the increase in systolic pressure that results from stiff vessel disease. In individuals with pulse pressure greater than 60 mm Hg there is an increased risk of death from cardiovascular morbidities. In a Phase Ia trial, one compound believed to work by a mechanism shared by the compounds of the invention, 3-[2-phenyl-2-oxoethyl]-4,5-dimethyl-thiazolium salt, reduced pulse pressure in elderly patients with pulse pressures greater than 60 mm Hg in a statistically significant manner. This decrease in pulse pressure was believed to be due primarily to the effect of the agent on lowering the systolic blood pressure.

The agents of the invention are used to treat, prevent, reduce or ameliorate reduced vascular compliance, elevated pulse pressure, and hypertension. Moreover, the agents are used to reduce pulse pressure, increase vascular compliance, or decrease the risk of death.

Heart Failure

Congestive Heart Failure (CHF) is a clinical syndrome that entails cardiac disease of the ventricle. Diastolic dysfunction is a subset of heart failure in which the left ventricle stiffens with age. The stiffening of the left ventricle that occurs in CHF and in diastolic dysfunction is believed to result from increased crosslinking of collagen fibers with age and/or fibrosis and related hypertrophy. First agents are used to treat, prevent, reduce or ameliorate heart failure.

Retinopathy

The effect of diabetes on the eye is called diabetic retinopathy and involves changes to the circulatory system of the retina. The earliest phase of the disease is known as background diabetic retinopathy wherein the arteries in the retina become weakened and leak, forming small, dot-like hemorrhages. These leaking vessels often lead to swelling or edema in the retina and decreased vision. The next stage is proliferative diabetic retinopathy, in which circulation problems cause areas of the retina to become oxygen-deprived or ischemic. New vessels develop as the circulatory system attempts to maintain adequate oxygen levels within the retina. Unfortunately, these new vessels hemorrhage easily. In the later phases of the disease, continued abnormal vessel growth and scar tissue may cause serious problems such as retinal detachment. First agents are used to treat, prevent, reduce or ameliorate diabetic retinopathy. The first agents can be administered by the methods described below, including by topical administration to the eye. The agents can also be administered by intravitreal implant.

Cataracts, Other Damage to Lens Proteins

AGE-mediated crosslinking and/or fibrotic processes are believed to contribute to cataract formation and formation of other damage to lens proteins. First agents are used to treat, prevent, reduce or ameliorate cataracts or other damage to lens proteins.

Alzheimer's Disease

Considerable evidence exists implicating AGEs that form in the neurofibrillary tangles (tau protein) and senile plaques (beta-amyloid peptide) in early neurotoxic processes of Alzheimer's disease. Insoluble human tau protein is likely crosslinked. Glycation of insoluble tau from AD patients and experimentally AGE-modified tau generate oxygen free radicals, resulting in the activation of transcription via nuclear factor-kappa B, and resulting in an increase in amyloid beta-protein precursor and release of amyloid beta-peptides. Thus, A.G.E.-modified tau may function as an initiator in a positive feedback loop involving oxidative stress and cytokine gene expression. First agents are used to treat, prevent, reduce or ameliorate Alzheimer's disease.

Other Indications

For reasons analogous to those set forth above, the invention is believed to be useful in treating, preventing, reducing or ameliorating diabetes or its associated adverse sequelae, and peripheral neuropathy. The agents, especially in topical form, increase elasticity and/or reduce wrinkles in skin. The agents further increase red blood cell deformability.

The method of the invention is used to treat animals, preferably mammals, preferably humans.

Unless otherwise specified, alkyl groups contain 1–6 carbon atoms and include methyl, ethyl, propyl, butyl, pentyl, hexyl, and the corresponding branched-chain isomers thereof. In some embodiments, the alkyl groups are $C_1$ to $C_3$. Similarly, the alkoxy groups contain from 1 to 6 carbon atoms, and include methoxy, ethoxy, propoxy, butoxy, pentoxy, and hexoxy, and the corresponding branched-chain isomers thereof. These groups are optionally substituted by one or more halo, hydroxy, amino or alkylamino groups.

The aryl groups are those containing 6–10 carbon atoms, such as naphthyl, phenyl and alkyl substituted-phenyl, e.g., tolyl and xylyl, and are optionally substituted by one to two halo, hydroxy, alkoxy or dialkylamino groups. Preferred aryl groups are phenyl, methoxyphenyl and 4-bromophenyl groups. Heteroaryl groups are 5 or 6 membered heteroaryl rings. The heteroaryl ring contains at least one and up to three atoms of N for the 6 membered heteroaryl ring. The 5 membered heteroaryl ring contains; (1) from one to three atoms of N, or (2) one atom of O or S and zero to two atoms of N. Nonlimiting examples of heteroaryl groups include: pyrrolyl, furranyl, thienyl, pyridyl, oxazolyl, pyrazolyl, pyrimidinyl, pyrazolyl, phthalazinyl, quinazolinyl and quinozalinyl. Aryls can be fused to either a benzene, pyridine, pyrimidine, pyridazine, or (1,2,3) triazine ring.

As used herein, $C_6$ or $C_{10}$ aryl groups and heterocycles containing 4 to 10 ring members are monocyclic or bicyclic. The ring fusions of the bicyclic heterocycles are at carbon—carbon bonds.

In certain embodiments of the invention, the thiazoliums and imidazoliums of the invention contain $R^2$ and $R^3$ substitutions that together with their ring carbons (the C4–C5 carbons of the thiazoliums and imidazoliums) form a fused C5 to C7 cycloalkyl ring having up to two double bonds including the fused double bond (the C4–C5 double bond of the thiazoliums and imidazoliums). The cycloalkyl ring can be substituted by one or more of the group consisting of alkyl, alkoxycarbonyl, amino, aminocarbonyl, carboxy, fluoro, and oxo substituents. One of ordinary skill in the art will recognized that where cycloalkyl groups contain double bonds, the sp2 hybridized carbon atoms can contain only one substituent (which can not be amino- or oxo-). $Sp^3$ hybridized carbon atoms in the cycloalkyl ring can be geminally substituted with the exception that (1) two amino groups and (2) one amino and one fluoro group can not be substituted on the same $sp^3$ hybridized carbon atom.

In certain embodiments of the invention, the thiazoliums and imidazoliums of the invention contain $R^2$ and $R^3$ substitutions that together with their ring carbons (the C4–C5 carbons of the thiazoliums and imidazoliums) form a five to eight membered heterocycle (i.e. a bicyclic heterocycle is formed). In these embodiments the heterocycle is preferably not aromatic. Particular compounds within these embodiments contain sulfur atoms in the ring fused to the thiazoliums and imidazoliums. These sulfur atoms in these particular compounds can exist in various oxidation states, as $S(O)_n$, where n is 0,1, or 2.

In certain embodiments of the invention, the thiazoliums and imidazoliums of the invention contain $R^2$ and $R^3$ substitutions that together with their ring carbons (the C4–C5 carbons of the thiazoliums and imidazoliums) form a five or six membered heteroaryl ring (i.e, a bicyclic aromatic heterocycle is formed). A preferred bicyclic aromatic heterocycle of the invention is a purine analog [Q is N and $R^2$ and $R^3$ together with their ring carbons (the C4 and C5 of the imidazolium ring) form a pyrimidine ring].

The halo atoms can be fluoro, chloro, bromo or iodo.

For the purposes of this invention, the compounds of formula (I) are formed as biologically and pharmaceutically acceptable salts. Useful salt forms are the halides, particularly the bromide and chloride, tosylates, methanesulfonates, brosylates, fumarates, maleates, succinates, acetates, mesitylenesulfonate salts, and the like. Other related salts can be formed using similarly non-toxic, and biologically and pharmaceutically acceptable anions. Useful salt forms include the halides (particularly bromides and chlorides), tosylates, methanesulfonates, brosylates, fumarates, maleates, succinates, acetates, mesitylenesulfonates, and the like. Other related salts can be formed using similarly non-toxic, and biologically or pharmaceutically acceptable anions.

Representative compounds of the present invention are the following (or salts thereof):
1-methyl-3-(2-cyanomethylene)-imidazolium bromide
3-(2-cyanomethylene)-4,5-dimethyl-thiazolium bromide
3-(2-cyanomethylene)-4,5-cyclopenteno-thiazolium bromide
3-(2-cyanomethylene)-4,5-cyclohexeno-thiazolium bromide
3-(2-cyanomethyl)-4-methyl-5-(2-hydroxyethyl)thiazolium bromide
1-methyl-3-(2-cyanomethyl)imidazolium bromide
3-(2-cyanomethyl)-4,5-dimethylthiazolium bromide
3-(2-cyanomethyl)-4,5-cyclopentenothiazolium bromide
3-(2-cyanomethyl)-4,5-cyclohexenothiazolium bromide
1methyl–3-(2-cyanomethyl)imidazolium bromide
1-vinyl-3-(2-cyanomethyl)imidazolium chloride
1-allyl-3-(2-cyanomethyl)imidazolium chloride
1-(4-acetylphenyl)-3-(2-cyanomethyl)iidazolium chloride
1 -phenyl-3-(2-cyanomethyl)imidazolium chloride
1-(4-methoxyphenyl)-3-(2-cyanomethyl)imidazolium chloride
1-(4-methoxycarbonylphenyl)-3-(2-cyanomethyl-imidazolium chloride
3-(2-cyanomethyl)-1-methylbenzimidazolium chloride
1,5-dicyclohexyl-3-(2-cyanomethyl)imidazolium bromide The above compounds are capable of inhibiting the formation of advanced glycosylation endproducts on target molecules, including, for instance, proteins, or are capable of breaking or reversing already formed advanced glycosylation endproducts on such proteins. The cross-linking of protein by formation of advanced glycosylation endproducts contributes to the entrapment of other proteins and results in the development in vivo of conditions such as reduced elasticity and wrinkling of the skin, certain kidney diseases, atherosclerosis, osteoarthritis and the like. Similarly, plant material that undergoes nonenzymatic browning deteriorates and, in the case of foodstuffs, become spoiled or toughened and, consequently, inedible, unpalatable or non-nutritious. Thus, the compounds employed in accordance with this invention inhibit this late-stage Maillard effect and intervene in the deleterious changes described above, and reduce the level of the advanced glycosylation endproducts already present in the protein material.

The rationale of the present invention is to use agents which block, as well as reverse, the post-glycosylation step, e.g., the formation of fluorescent chromophores and cross-links, the presence of which is associated with, and leads to adverse sequelae of diabetes and aging. An ideal agent would prevent the formation of such chromophores and of cross-links between protein strands and trapping of proteins onto other proteins, such as occurs in arteries and in the kidney, and reverse the level of such cross-link formation already present.

The chemical nature of the early glycosylation products with which the compounds of the present invention are believed to react can vary. Accordingly the term "early glycosylation product(s)" as used herein is intended to include any and all such variations within its scope. For example, early glycosylation products with carbonyl moieties that are involved in the formation of advanced glycosylation endproducts, and that can be blocked by reaction with the compounds of the present invention, have been postulated. In one embodiment, the early glycosylation product can comprise the reactive carbonyl moieties of Amadori products or their further condensation, dehydration and/or rearrangement products, which can condense to form advanced glycosylation endproducts. In another scenario, reactive carbonyl compounds, containing one or more carbonyl moieties (such as glycolaldehyde, glyceraldehyde or 3-deoxyglucosone) can form from the cleavage of Amadori or other early glycosylation endproducts, and by subsequent reactions with an amine or Amadori product, can form carbonyl containing advanced glycosylation products such as alkylformyl-glycosylpyrroles.

Several investigators have studied the mechanism of advanced glycosylation product formation. In vitro studies by Eble et al., (1983), "Nonenzymatic Glucosylation and Glucose-dependent Cross-linking of Protein", J. Biol. Chem., 258:9406–9412, concerned the cross-linking of glycosylated protein with nonglycosylated protein in the absence of glucose. Eble et al. sought to elucidate the mechanism of the Maillard reaction and accordingly conducted controlled initial glycosylation of RNase as a model system. In one aspect, the glycosylated protein material was isolated and placed in a glucose-free environment and observed to determine the extent of cross-linking. Eble et al. observed that cross-linking continued to occur not only with the glycosylated protein but with non-glycosylated proteins as well. One of the observations was that the reaction between glycosylated protein and the protein material appeared to occur at the location on the amino acid sidechain of the protein. Confirmatory experimentation demonstrated that free lysine competed with the lysine on RNase for the binding of glycosylated protein.

While not wishing to be bound by any particular theory as to the mechanism by which the compounds of the instant invention reverse already formed advanced glycosylation endproducts, studies have been structured to elucidate a possible mechanism. Earlier studies examining the fate of the Amadori product (AP) in vivo have identified one likely route that could lead to the formation of covalent, glucose-derived protein crosslinks. This pathway proceeds by dehydration of the AP via successive beta-eliminations as shown in the Scheme A of U.S. Pat. No. 5,853,703. Thus, loss of the 4-hydroxyl of the AP (1) gives a 1,4-dideoxy-1-alkylamino-2,3-hexodiulose (AP-dione) (2). An AP-dione with the structure of an amino-1,4-dideoxyosone has been isolated by trapping model APs with the AGE-inhibitor aminoguanidine. Subsequent elimination of the 5-hydroxyl gives a 1,4,5-trideoxy-1-alkylamino-2,3-hexulos-4-ene (AP-ene-dione) (3), which has been isolated as a triacetyl derivative of its 1,2-enol form. Amadori-diones, particularly the AP-ene-dione, would be expected to be highly reactive toward protein crosslinking reactions by serving as targets for the addition of the amine (Lys, His)-, or sulfhydryl (Cys)-based nucleophiles that exist in proteins, thereby producing stable crosslinks of the form (4) as illustrated in U.S. Pat. No. 5,853,703.

Note that the linear AP-ene-dione of (3) and the stable cross-link of (4) can cyclize to form either 5- or 6-member lactol rings. See, the scheme shown in U.S. Pat. No. 5,853,703.

The possibility that a major pathway of glucose-derived crosslink formation proceeds through an AP-ene-dione intermediate was investigated by experiments designed to test the occurrence of this pathway in vivo as well as to effect the specific cleavage of the resultant $\alpha$-dicarbonyl-based protein crosslinks. Without being limited to theory, the imidazolium compounds of the invention are believed to act as "bidentate" nucleophiles, particularly designed to effect a carbon—carbon breaking reaction between the two carbonyls of the crosslink, in a similar manner to Scheme B of U.S. Pat. No. 5,853,703.

The present invention likewise relates to methods for inhibiting the formation of advanced glycosylation endproducts, and reversing the level of already formed advanced glycosylation endproducts, which comprise contacting the target molecules with a composition of the present invention. In the instance where the target proteins are contained in foodstuffs, whether of plant or animal origin, these foodstuffs could have applied to them by various conventional means a composition containing the present agents.

In the food industry, sulfites were found years ago to inhibit the Maillard reaction and are commonly used in processed and stored foods. Recently, however, sulfites in food have been implicated in severe and even fatal reactions in asthmatics. As a consequence, the sulfite treatment of fresh fruits and vegetables has been banned. The mechanism for the allergic reaction is not known. Accordingly, the present compositions and agents offer a nontoxic alternative to sulfites in the treatment of foods in this manner.

The present methods and compositions hold the promise for arresting, and to some extent reversing, the aging of key proteins both in animals and plants, and concomitantly, conferring both economic and medical benefits as a result thereof. In the instance of foodstuffs, the administration of the present composition holds the promise for retarding food spoilage thereby making foodstuffs of increased shelf life and greater availability to consumers. Replacement of currently-used preservatives, such as sulfur dioxide known to cause allergies and asthma in humans, with nontoxic, biocompatible compounds is a further advantage of the present invention.

The therapeutic implications of the present invention relate to the arrest, and to some extent, the reversal of the aging process which has been identified and exemplified in the aging of key proteins by advanced glycosylation and cross-linking. Thus, body proteins, and particularly structural body proteins, such as collagen, elastin, lens proteins, nerve proteins, kidney glomerular basement membranes and other extravascular matrix components would all benefit in their longevity and operation from the practice of the present invention. The present invention thus reduces the incidence of pathologies involving the entrapment of proteins by cross-linked target proteins, such as retinopathy, cataracts, diabetic kidney disease, glomerulosclerosis, peripheral vascular disease, arteriosclerosis obliterans, neuropathy (such as peripheral neuropathy), stroke, hypertension, atherosclerosis, osteoarthritis, periarticular rigidity, loss of elasticity and wrinkling of skin, stiffening of joints, glomerulonephritis and the like. Likewise, all of these conditions are in evidence and tend to occur at an accelerated rate in patients afflicted with diabetes mellitus as a consequence of this hyperglycemia. Thus, the present therapeutic method is relevant to treatment of these and related conditions in patients either of advanced age or those suffering from one of the mentioned pathologies.

Protein cross-linking through advanced glycosylation product formation can decrease solubility of structural proteins such as collagen in vessel walls and can also trap serum proteins, such as lipoproteins to the collagen. Also, this can result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia is believed to result from excessive formation of glucose-derived cross-links. Such diabetic microvascular changes and microvascular occlusion can be effectively prevented and reversed by chemical inhibition and reversal of the advanced glycosylation product formation utilizing a composition and the methods of the present invention.

Molecular cross-linking through advanced glycosylation product formation can decrease solubility of structural proteins such as collagen in vessel walls and can also trap serum proteins, such as lipoproteins to the collagen. Also, this can result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia has been hypothesized to result from excessive formation of sugar-derived and particularly, glucose-derived cross-links. Such diabetic microvascular changes and microvascular occlusion can be effectively prevented and reversed by chemical inhibition and reversal of the advanced glycosylation product formation utilizing compositions and the methods of the present invention.

Studies indicate that the development of chronic diabetic damage in target organs is primarily linked to hyperglycemia so that tight metabolic control would delay or even prevent end-organ damage. See Nicholls et al., Lab. Invest., 60, No. 4, p. 486 (1989), which discusses the effects of islet isografting and aminoguanidine in murine diabetic nephropathy. These studies further evidence that aminoguanidine diminishes aortic wall protein cross-linking in diabetic rats and confirm earlier studies by Brownlee et al., Science, 232:1629–1632 (1986) to this additional target organ of complication of diabetes. Also, an additional study showed the reduction of immunoglobulin trapping in the kidney by aminoguanidine (Brownlee et al., Diabetes, (1):42A (1986)).

Further evidence in the streptozotocin-diabetic rat model that aminoguanidine administration intervenes in the development of diabetic nephropathy was presented by Brownlee et al., Science, 232:1629–1632 (1986), with regard to morphologic changes in the kidney which are hallmarks of diabetic renal disease. These investigators reported that the increased glomerular basement membrane thickness, a major structural abnormality characteristic of diabetic renal disease, was prevented with aminoguanidine.

Taken together, these data strongly suggest that inhibition and reversal of the formation of advanced glycosylation endproducts (AGEs), by the teaching of the present invention, can prevent, as well as to some extent reverse late, as well as early, structural lesions due to diabetes, as well as changes during aging caused by the formation of AGEs.

Diabetes-induced changes in the deformability of red blood cells, leading to more rigid cell membranes, is another manifestation of cross-linking and aminoguanidine has been shown to prevent, treat or reverse such changes in vivo. In such studies, New Zealand White rabbits with induced, long-term diabetes are used to study the effects of a test compound on red blood cell (RBC) deformability (df). The test compound is administered at a rate of 100 mg/kg by oral gavage (tube delivery to stomach) to diabetic rabbits.

A further consequence of diabetes is the hyperglycemia-induced matrix bone differentiation resulting in decreased bone formation usually associated with chronic diabetes. In animal models, diabetes reduces matrix-induced bone differentiation by 70%.

In the instance where the compositions of the present invention are utilized for in vivo or therapeutic purposes, it can be noted that the compounds or agents used therein are biocompatible. Pharmaceutical compositions can be prepared with a therapeutically effective quantity of the agents or compounds of the present invention and can include a pharmaceutically acceptable carrier, selected from known materials utilized for this purpose. To treat the indications of the invention, an effective amount of a pharmaceutical compound will be recognized by clinicians but includes an amount effective to treat, reduce, ameliorate, eliminate or prevent one or more symptoms of the disease sought to be treated or the condition sought to be avoided or treated, or to otherwise produce a clinically recognizable change in the pathology of the disease or condition. Such compositions can be prepared in a variety of forms, depending on the method of administration. Also, various pharmaceutically acceptable addition salts of the compounds of the invention can be utilized.

Pharmaceutical compositions can be prepared to allow a therapeutically effective quantity of the compound of the present invention, and can include a pharmaceutically acceptable carrier, selected from known materials utilized for this purpose. See, e.g., Remington, The Science and Practice of Pharmacy, 1995; Handbook of Pharmaceutical Excipients, 3$^{rd}$ Edition, 1999. Such compositions can be prepared in a variety of forms, depending on the method of administration, such as sublingual, rectal, nasal, vaginal, topical (including the use of a patch or other transdermal delivery device), by pulmonary route by use of an aerosol, or parenteral, including, for example, intramuscular, subcutaneous, intraperitoneal, intraarterial, intravenous or intrathecal.

In addition to the subject compound, the compositions of this invention can contain a pharmaceutically-acceptable carrier. The term "pharmaceutically-acceptable carrier", as used herein, means one or more compatible solid or liquid filler diluents or encapsulating substances that are suitable for administration to an animal, including a mammal or human. The term "compatible", as used herein, means that the components of the composition are capable of being commingled with the subject compound, and with each other, such that there is no interaction that would substantially reduce the pharmaceutical efficacy of the composition under ordinary use. Preferably when liquid dose forms are used, the compounds of the invention are soluble in the components of the composition. Pharmaceutically-acceptable carriers should, of course, be of sufficiently high purity and sufficiently low toxicity to render them suitable for administration to the animal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically- acceptable carrier to be used in conjunction with the subject compound is basically determined by the way the compound is to be administered. If the subject compound is to be injected, the preferred pharmaceutically-acceptable carrier is sterile, physiological saline, with a blood-compatible suspending agent, the pH of which has been adjusted to about 7.4.

If the preferred mode of administering the subject compound is perorally, the preferred unit dosage form is therefore tablets, capsules, lozenges, chewable tablets, and the like. Such unit dosage forms comprise a safe and effective amount of the subject compound, which is preferably from about 0.7 or 3.5 mg to about 280 mg/70 kg, more preferably from about 0.5 or 10 mg to about 210 mg/70 kg. The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder-mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.012% to about 0.933% of the subject compound, more preferably from about 0.033% to about 0.7%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Compositions can also be used to deliver the compound to the site where activity is desired; such as eye drops, gels and creams for ocular disorders.

Compositions of this invention include solutions or emulsions, preferably aqueous solutions or emulsions comprising a safe and effective amount of a subject compound intended for topical intranasal administration. Such compositions preferably comprise from about 0.01% to about 10.0% w/v of a subject compound, more preferably from about 0.1% to about 2.0%. Similar compositions are preferred for systemic delivery of subject compounds by the intranasal route. Compositions intended to deliver the compound systemically by intranasal dosing preferably comprise similar amounts of a subject compound as are determined to be safe and effective by peroral or parenteral administration. Such compositions used for intranasal dosing also typically include safe and effective amounts of preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acids and bases to adjust the pH of these aqueous compositions as needed. The compositions may also comprise local anesthetics or other actives. These compositions can be used as sprays, mists, drops, and the like.

Other preferred compositions of this invention include aqueous solutions, suspensions, and dry powders comprising a safe and effective amount of a subject compound intended for atomization and inhalation administration. Such compositions are typically contained in a container with attached atomizing means. Such compositions also typically include propellants such as chlorofluorocarbons 12/11 and 12/114, and more environmentally friendly fluorocarbons, or other nontoxic volatiles; solvents such as water, glycerol and ethanol, including cosolvents as needed to solvate or suspend the active agent; stabilizers such as ascorbic acid, sodium metabisulfite; preservatives such as cetylpyridinium chloride and benzalkonium chloride; tonicity adjustors such as sodium chloride; buffers; and flavoring agents such as sodium saccharin. Such compositions are useful for treating respiratory disorders, such as asthma and the like.

Other preferred compositions of this invention include aqueous solutions comprising a safe and effective amount of a subject compound intended for topical ocular administration. Such compositions preferably comprise from about 0.01% to about 0.8% w/v of a subject compound, more preferably from about 0.05% to about 0.3%. Such compositions also typically include one or more of preservatives, such as benzalkonium chloride or thimerosal; vehicles, such as poloxamers, modified celluloses, povidone and purified water; tonicity adjustors, such as sodium chloride, mannitol and glycerin; buffers such as acetate, citrate, phosphate and borate; antioxidants such as sodium metabisulfite, butylated hydroxy toluene and acetyl cysteine; acids and bases can be used to adjust the pH of these formulations as needed.

Other preferred compositions of this invention useful for peroral administration include solids, such as tablets and capsules, and liquids, such as solutions, suspensions and emulsions (preferably in soft gelatin capsules), comprising a safe and effective amount of a subject compound. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit™ coatings, waxes and shellac.

The compounds of the invention are administered by ocular, oral, parenteral, including, for example, using formulations suitable as eye drops. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. See, Remington's Pharmaceutical Sciences, 16th Ed., Mack Publishing, Easton, Pa., 1980, as well as later editions, for information on pharmaceutical compounding.

Numerous additional administration vehicles will be apparent to those of ordinary skill in the art, including without limitation slow release formulations, liposomal formulations and polymeric matrices.

In another preferred embodiment, the pharmaceutically effective amount is approximately 0.1 or 0.5 to 4 mg/kg body weight daily. Still more preferably, the pharmaceutically effective amount is approximately 1 mg/kg body weight daily. In a preferred embodiment, the amount is administered in once daily doses, each dose being approximately 1 mg/kg body weight.

The activity of the compounds of the invention in breaking, reversing or inhibiting the formation of AGE's or AGE-mediated crosslinks can be assayed by any of the methods described in U.S. Pat. No. 5,853,703.

In one embodiment, the compounds of the invention are used to reduce, minimize, or reverse the damage caused by intraperitoneal dialysis, In intraperitoneal dialysis, the dialysis solutions contain high levels of carbohydrates, and are known to damage intraperitoneal tissue by forming AGE crosslinks which lead to loss of membrane function. Effective amounts of compounds of the invention can be incorporated in such dialysis solutions, or separately perfused through the intraperitoneal cavity. Such effective amounts range, for example, from about 2 mg/L to 100 mg/L of a solution bathing the intraperitoneal cavity.

In another embodiment, the invention discloses classes of compounds that can also reverse the cardiovascular stiffness associated with normal aging in mammals. By breaking established A.G.E. cross-links, it is believed that these classes of compounds modify diastolic stiffness associated with the left ventricle. See, M. Asif et al, *Proc. Natl. Acad. Sci. USA* 97, 2809–2813, 2000, describing similar activity for another class of compounds. As a result, cardiac function significantly improves, as evidenced by increased left ventricular (LV) end diastolic volume (EDV), stroke volume, and decreased end diastolic pressure (EDP). While it is believed that the method of the present invention is accomplished by the above described mechanism, the possibility that the method of the present invention improves myocardial elasticity through alternative mechanisms is not ruled out.

The present invention provides for methods that can be used to monitor hemodynamic indicators of myocardial elasticity. These indicators can be used to monitor subjects during the course of therapy of compound administration, and they can also be used to identify patients that are candidates for the method of the present invention. Useful hemodynamic indicators of myocardial elasticity include left ventricular end-diastolic volume (EDV), stroke volume, end-diastolic pressure (EDP), and left ventricular stiffness.

Left ventricular stiffness is a preferred measure of myocardial elasticity. This parameter can be calculated from the end-diastolic volume (EDV) and the end-diastolic pressure (EDP). These two parameters can be determined experimentally in dogs. One method useful for the measurements in dogs involves the introduction of catheters into the left ventricular (LV) chamber and proximal aorta via the carotid artery. Goodale-Lubin catheters (no. 8 French), for example, can be used. Transducers with a suitable physiological recording system using pressure amplifiers and a fluid-filled catheter system optimally damped for frequency-response can record LV and arterial pressures. Typically the transducers are placed at the mid-thoracic level and balanced to provide for equal sensitivity. In animals the invention provides for measurement of EDV and EDP after intravascular volume loading. Typically the increased intravascular loading is accomplished through administration of 10% dextran-40. Preferably the infusion rate of the loading agent is 3 ml-min$^{-1}$-kg-1 over 3 min. In the intact animal, simultaneous measures of LV pressure and volume can be made before and after volume loading. EDP can be measured from pressure determinations at the end-expiration phase of the respiratory cycle.

LV volume can be determined by two-dimensional echocardiography. In a preferred embodiment, imaging location and time-gain settings are adjusted to yield optimal definition of endocardial borders, which can be delineated by bubbling saline into the LV chamber. Preferably the influence of heart rate on these measurements is minimized, by comparing ventricular dimensions at similar R—R intervals. In a preferred embodiment this comparison is made using an Ultramark 4 system (Advanced Technology Laboratories). The end-diastolic and end-systolic dimensions for three to four consecutive cardiac cycles can be measured and averaged, and the ejection fraction and stroke volume subsequently calculated. Ventricular volume can be derived by the length-diameter method (Vuille, C. & Weyman, A. E. (1994) In *Principles and Practice of Echocardiography*, ed. Weyman, A. E. (Lea & Gebiger, Philadelphia), pp. 575–624), with apical views for measurements taken from the inner margins of the endocardial echoes. Endocardial and epicardial borders can be traced directly from the video display onto a digitizing tablet. End-diastolic frames can be selected for analysis by using the R wave as a marker for end diastole.

To characterize the diastolic pressure-volume relationship in the left ventricle (Gaasch, W. H. (1994) in *Left Ventricular Diastolic Dysfunction and Heart Failure*, eds. Gaasch, W. H. & Lewinter, M. M. (Lea & Febiger, Philadelphia), pp. 143–149), the exponential equation $P=be^{kV}$ can be used, where P=pressure in mmHg, V=volume in ml/kg, b=the pressure intercept in mmHg, and k represents the modulus of chamber stiffness in the intact ventricle. Two coordinates of pressure and volume can be used. Typically the early diastolic coordinates consist of the lowest value of diastolic pressure before the mitral valve opens and the end systolic volume. EDP and volume can then be utilized as the second coordinates. The chamber-stiffness constant k is calculated as the slope of the natural logarithm of pressure to volume: $\ln(P)=kV+\ln(b)$. Chamber stiffness is derived from the relation $dP/dV=kP$. With a progressive increase in volumes calculated, myocardial stiffness would be expected to increase as a preload- dependent phenomenon (Kato, S., Spinale, F. G., Tanaka, R., Johnson, W., Cooper, I. V. G. & Zile, M. R. (1995) *Am. J. Physiol.* 269 H863-H868). Myocardial stiffness can be calculated from E=kstress.

In a preferred embodiment subjects for the method of the invention are free of valvular or pericardial disease. Typically this assessment can be determined by echocardiography.

The invention is useful in treating or preventing damage to cardiovascular tissue, including myocardial tissue, in heart failure (e.g., congestive heart failure). The method can comprise administering an effective amount of the one or more compounds to improve myocardial elasticity or reduce any loss of myocardial elasticity in heart failure. As noted in the Merck Manual, Seventeenth Edition, Heart failure (congestive heart failure) can be described as symptomatic myocardial dysfunction resulting in a characteristic pattern of hemodynamic, renal, and neurohormonal responses. Congestive heart failure (CHF) develops when plasma volume increases and fluid accumulates in the lungs, abdominal organs (especially the liver), and peripheral tissues. The clinical manifestations of HF may reflect impairment of the left or right ventricle. Left ventricular (LV) failure characteristically develops in coronary artery disease, hypertension, and most forms of cardiomyopathy and with congenital defects (eg, ventricular septal defect, patent ductus arteriosus with large shunts). Right ventricular (RV) failure is most commonly caused by prior LV failure (which increases pulmonary venous pressure and leads to pulmonary arterial hypertension) and tricuspid regurgitation. Mitral stenosis, primary pulmonary hypertension, multiple pulmonary emboli, pulmonary artery or valve stenosis, and RV infarction are also causes. Volume overload and increased systemic venous pressure may also occur in polycythemia or overtransfusion, acute renal failure with overhydration, and obstruction of either vena cava simulating HF. In these conditions, myocardial function may be normal.

HF is manifest by systolic or diastolic dysfunction, or both. Combined systolic and diastolic abnormalities are common. In systolic dysfunction (primarily a problem of ventricular contractile dysfunction), the heart fails to provide tissues with adequate circulatory output. A wide variety of defects in energy utilization, energy supply, electrophysiologic functions, and contractile element interaction occur, which appear to reflect abnormalities in intracellular $Ca^{++}$ modulation and cyclic adenosine monophosphate (cAMP) production. Diastolic dysfunction (resistance to ventricular filling not readily measurable at the bedside) accounts for 20 to 40% of cases of HF. It is generally associated with prolonged ventricular relaxation time, as measured during isovolumic relaxation (the time between aortic valve closure and mitral valve opening when ventricular pressure falls rapidly). Resistance to filling (ventricular stiffness) directly relates to ventricular diastolic pressure; this resistance increases with age, probably reflecting myocyte loss and increased interstitial collagen deposition. Diastolic dysfunction is presumed to be dominant in hypertrophic cardiomyopathy, circumstances with marked ventricular hypertrophy (eg, hypertension, advanced aortic stenosis), and amyloid infiltration of the myocardium. High output failure is HF associated with a persistent high CO that eventually results in ventricular dysfunction. Conditions associated with high CO include anemia, beriberi, thyrotoxicosis, pregnancy, advanced Paget's disease, and arteriovenous fistula. CHF may develop in high-output states but is often reversible by treating the underlying cause. CO is elevated in various forms of cirrhosis, but the onset of congestion reflects cardiac and hepatic mechanisms of fluid retention.

The invention also extends to a method of inhibiting and reversing the discoloration of teeth resulting from nonenzymatic browning in the oral cavity which comprises administration to a subject in need of such therapy an amount effective to inhibit and reverse the formation of advanced glycosylation endproducts of a composition comprising an agent of the invention.

The nonenzymatic browning reaction which occurs in the oral cavity results in the discoloration of teeth. Presently used anti-plaque agents accelerate this nonenzymatic browning reaction and further the staining of the teeth. Recently, a class of cationic anti-microbial agents with remarkable anti-plaque properties have been formulated in oral rinses for regular use to kill bacteria in the mouth. These agents, the cationic antiseptics, include such agents as alexidine, cetyl pyridinium chloride, chlorhexidine gluconate, hexetidine, and benzalkonium chloride.

Tooth staining by chlorhexidine and other anti-plaque agents apparently results from the enhancement of the Maillard reaction. Nordbo, J. Dent. Res., 58:1429 (1979) reported that chlorhexidine and benzalkonium chloride catalyze browning reactions in vitro. Chlorhexidine added to mixtures containing a sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products.

In accordance with this method, the compounds of the invention are formulated into compositions adapted for use in the oral cavity. Particularly suitable formulations are oral rinses and toothpastes incorporating the active agent.

In the practice of this invention, conventional formulating techniques are utilized with nontoxic, pharmaceutically acceptable carriers typically utilized in the amounts and combinations that are well-known for the formulation of such oral rinses and toothpastes.

The agents of the invention are formulated in compositions in an amount effective to inhibit and reverse the formation of advanced glycosylation endproducts. This amount will, of course, vary with the particular agent being utilized and the particular dosage form, but typically is in the range of 0.01% to 1.0%, by weight, of the particular formulation.

The novel compounds of the formula I can be prepared by modification of syntheses well known in the art. The novel compounds are those of the formula I

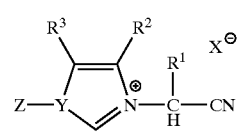

I wherein the substituent groups are as described above.

A useful synthetic route for the preparation of compounds of formula I is shown in Scheme I.

Scheme I

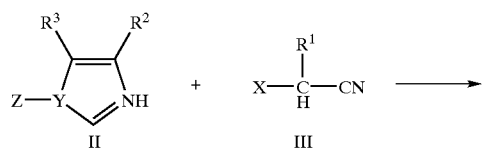

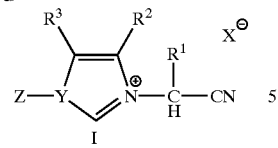

wherein $R^1$, $R^2$, $R^3$, Y and Z are as described in the text above, and X is a halide, mesitylenesulfonate or other biologically acceptable anion. In Scheme I, the appropriately substituted imidazole or thiazole of formula II is contacted with a halo substituted acetonitrile of formula III to produce the compounds of formula I. The reaction can be performed without any added solvent, or an anhydrous solvent can be utilized as the solvent medium. When a solvent is used, acetonitrile is a typical solvent for this reaction. Reaction times vary according to particular reactants and conditions but are usually in the range of a few minutes to 48 hours at a temperature of 25–130° C.

In another synthesis, the preparation of compounds of the formula I wherein $R^3$ is —$CH_2OH$ are exemplified. Formamide is first converted to thioformamide by reaction with phosphorus pentasulfide. Thioformamide is reacted with ethyl 2-chloroacetoacetate in dry dioxane as follows:

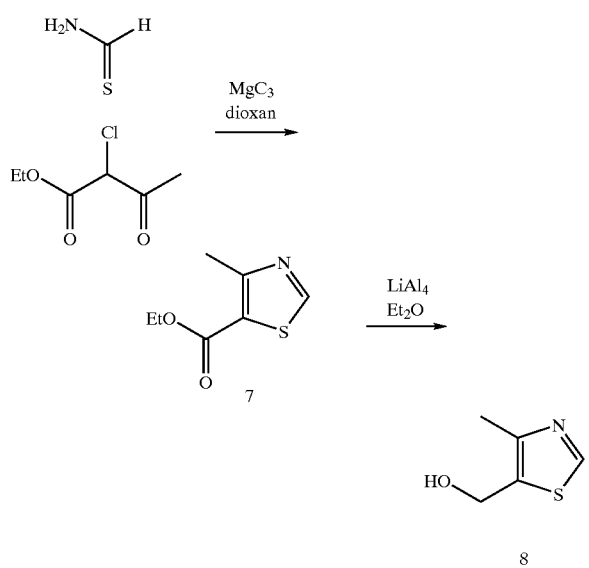

Compound 8 can then be reacted with a suitable alkylating agent to make a compound of the invention.

Where $R^2$ is —$CH_2OH$ and $R^3$ is —$CH_3$ in Formula I, the route shown below can be used. The preparation of a thiazole analog containing a 4-hydroxymethyl group, for example, is shown below:

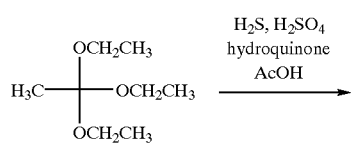

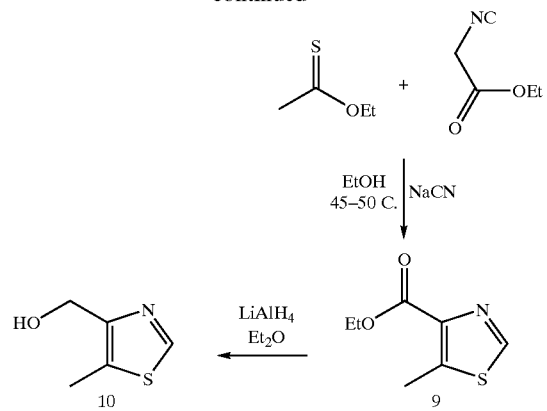

Compound 10 can then be alkylated with a suitable alkylating agent to make a compound of the invention.

Note that reaction conditions indicated in the various reaction schemes are exemplary: such conditions as solvent and temperature are subject to modification within ordinary skill.

EXAMPLE 1

Preparation of 1-methyl-3-(2-cyanomethylene)-imidazolium Bromide

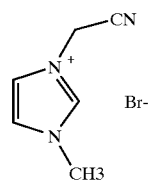

A mixture of 1-methylimidazole (1 g, 12.2 mmol) and bromoacetonitrile (1.46 g, 12.2 mmol) were combined and stirred. An exothermic reaction was produced and the product precipitated from the reaction mixture. After cooling the reaction mixture is allowed to cool to room temperature acetonitrile ($CH_3CN$) (2 mL) is added. The crude product is recovered by filtration and washed with additional $CH_3CN$. The crude product is dissolved in $H_2O$, treated with decolorizing carbon and evaporated in vacuo to 5 dryness. The product is further purified by recrystallization from a mixture of ethanol (EtOH), $CH_3CN$ and diethyl ether to yield 1-methyl-3-(2-cyanomethylene)-imidazolium bromide as a white crystalline solid: mp 165–167° C.

EXAMPLE 2

Preparation of 3-(2-cyanomethylene)-4,5-dimethyl-thiazolium Bromide

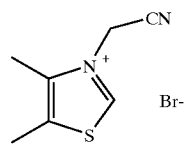

A mixture of 4,5-dimethylthiazole and bromoacetonitrile were heated with stirring at 95° C. for 1 hour. The product precipitated from the mixture within 30 minutes. After cooling to room temperature, the product a solution of 30% v/v of diethyl ether: $CH_3CN$ (10 mL) was added with stirring. The crude product was recovered by filtration, and recrystallized from a mixture of EtOH and $CH_3CN$ to yield 2.136 g of 3-(2-cyanomethylene)-4,5-dimethyl-thiazolium bromide as needles: mp 184–186° C.(dec.).

EXAMPLE 3

Preparation of 3-(2-cyanomethylene)-4,5-cyclohexeno-thiazolium Bromide

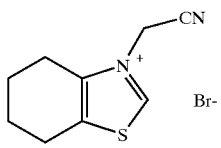

A mixture of thioformamide (0.8 g), 2-chlorocyclohexan-1-one (1.73 g), $MgCO_3$ (1.5 g) was refluxed in dioxane (12 mL) for 30 h. The reaction mixture was evaporated in vacuo, and the concentrated poured into diethyl ether (30 mL). The resulting ethereal solution was washed with 1% NaOH solution (3×15 mL). The combined NaOH solution was back extracted with diethyl ether. The ether layers were combined, washed with saturated NaCl soution until neutral, and then dried over $Na_2SO_4$. The ethereal solution was evaporated in vacuo to afford 1.02 g of 4,5-cyclohexenothiazole.

A mixture of 4,5-cyclohexenothiazole (1 g, 7.2 mmol) and bromoacetonitrile (0.863 g, 7.2 mmol) were heated at 120° C. for 1 h. After cooling the reaction mixture was treated with a solution of 30% diethyl ether in $CH_3CN$ (10 mL). The product was recovered by filtration and washed with additional 30% diethyl ether in $CH_3CN$. The product was recrystallized from a mixture of EtOH and $CH_3CN$ to yield 0.752 g of 3-(2-cyanomethylene)-4,5-cyclohexeno-thiazolium bromide as a crystalline solid: mp 215–217° C. (dec.).

EXAMPLE 4

Preparation of 3-(2-cyanomethylene)-4,5-cyclopenteno-thiazolium Bromide

The preparation of 3-(2-cyanomethylene)-4,5-cyclopenteno-thiazolium bromide from 2-chlorocyclopentan-1-one is conducted as in the above procedure.

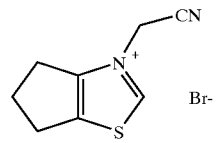

EXAMPLE 5

| | mg/tablet |
|---|---|
| Compound of Invention | 50 |
| Starch | 50 |

| | mg/tablet |
|---|---|
| Mannitol | 75 |
| Magnesium stearate | 2 |
| Stearic acid | 5 |

The compound, a portion of the starch and the lactose are combined and wet granulated with starch paste. The wet granulation is placed on trays and allowed to dry overnight at a temperature of 45° C. The dried granulation is comminuted to a particle size of approximately 20 mesh. Magnesium stearate, stearic acid and the balance of the starch are added and the entire mix blended prior to compression on a suitable tablet press. The tablets are compressed at a weight of 232 mg. using a $^{11}\!/_{32}''$ punch with a hardness of 4 kg. These tablets disintegrate within a half hour according to the method described in USP XVI.

EXAMPLE 6

| Lotion | mg/g |
|---|---|
| Compound of Invention | 1.0 |
| Ethyl alcohol | 400.0 |
| Polyethylene glycol 400 | 300.0 |
| Hydroxypropyl cellulose | 5.0 |
| Propylene glycol | to make 1.0 g |

EXAMPLE 7

| Oral Rinse | |
|---|---|
| Compound of Invention | 1.4% |
| Chlorhexidine gluconate | 0.12% |
| Ethanol | 11.6% |
| Sodium saccharin | 0.15% |
| FD&C Blue No. 1 | 0.001% |
| Peppermint Oil | 0.5% |
| Glycerine | 10.0% |
| Tween 60 | 0.3% |
| Water to | 100% |

EXAMPLE 8

| Toothpaste | |
|---|---|
| Compound of Invention | 5.5% |
| Sorbitol, 70% in water | 25% |
| Sodium saccharin | 0.15% |
| Sodium lauryl sulfate | 1.75% |
| Carbopol 934, 6% dispersion in | 15% |
| Oil of Spearmint | 1.0% |
| Sodium hydroxide, 50% in water | |
| Dibasic calcium phosphate dihydrate | 45% |
| Water to | 100% |

EXAMPLE 9

Cross-Linking Inhibition Assay

Inhibition of cross-linking is assayed as described in U.S. Pat. No. 5,853,703.

EXAMPLE 10

Cross-Link Breaking Assay

The breaking of cross-links is assayed as described in U.S. Pat. No. 5,853,703.

EXAMPLE 11

Measurement of IgG Crosslinked to Red Blood Cells

IgG crosslinked to red blood cells, and inhibition of such crosslinking in animals to which a compound of the invention has been administered are assayed as described in U.S. Pat. No. 5,853,703.

EXAMPLE 12

Effects on Collagen

The effects on collagen of administering to an animal a compound of the invention can be assessed as described in U.S. Pat. No. 5,853,703.

The meaning of "effective amount" will be recognized by clinicians but includes an amount effective to (1) reduce, ameliorate or eliminate one or more symptoms of the disease sought to be treated, (2) induce a pharmacological change relevant to treating the disease sought to be treated, or (3) prevent or lessen the frequency of occurrence of a disease. In certain embodiments, should the compound at issue have glucose lowering activity, the amount is preferably less than a glucose lowering effective amount.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods can be used and that it is intended that the invention can be practiced otherwise than as specifically described herein. Accordingly, this invention includes all modifications encompassed within the spirit and scope of the invention as defined by the claims that follow.

What is claimed is:

1. A compound of the formula:

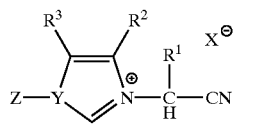

wherein

Y is N;

Z is an alkyl group of 1 to 7 carbon atoms, vinyl, allyl, arylcarbonyl, amino or alkoxycarbonylalkyl, or Z is according to the formula $-CH(R^4)(CN)$, or Z is $-CH_2C(=O)R^5$, where $R^5$ is (a) a $C_6-C_{10}$ aryl group, said aryl group optionally substituted by one or more alkyl, alkoxy, halo, dialkylamino, hydroxy, nitro or $C_1-C_2$ alkylenedioxy groups or (b) heterocyclic group containing 4–10 ring members and 1–3 heteroatoms selected from the group consisting of oxygen, nitrogen and sulfur wherein the heterocyclic group is optionally substituted by one or more substituents selected from the group consisting of alkyl, oxo, alkoxycarbonylalkyl, aryl, and aralkyl group, and the one or more substituents are optionally substituted by one or more alkyl or alkoxy groups, $R^1$ and $R^4$ are independently hydrogen, alkyl or phenyl optionally substituted with one or more halogen, alkyl, di(lower alkyl)amino or alkoxy groups; and $R^2$ and $R^3$ are:

1. independently selected from hydrogen, acylamino, acyloxyalkyl, alkanoyl, alkanoylalkyl, alkenyl, alkoxy, alkoxycarbonyl, alkoxycarbonylalkyl, alkyl, alkylamino, $(C_1-C_3)$alkylenedioxy, allyl, amino, ω-alkylenesulfonic acid, carbamoyl, carboxy, carboxyalkyl, cycloalkyl, dialkyl amino, halo, hydroxy, $(C_2-C_6)$hydroxyalkyl, mercapto, nitro, sulfamoyl, sulfonic acid, alkylsulfonyl, alkylsulfinyl, alkylthio, trifluoromethyl, azetidin-1-yl, niorpholin-4-yl, thiomorpholin 4-yl, piperidin-1-yl, 4-[$C_6$ or $C_{10}$]arylpiperidin-1-yl, 4-[$C_6$ or $C_{10}$]arylpiperazin-1-yl, Ar {wherein, consistent with the rules of aromaticity, Ar is $C_6$ or $C_{10}$ aryl or a 5- or 6-membered heteroaryl ring, wherein 6-membered heteroaryl ring contains one to three atoms of N, and the 5-membered heteroaryl ring contains from one to three atoms of N or one atom of O or S and zero to two atoms of N, each heteroaryl ring is optionally fused to a benzene, pyridine, pyrimidine, pyridazine, pyrazine, or (1,2,3)triazine (wherein the ring fusion is at a carbon—carbon double bond of Ar)}, Ar-alkyl, Ar-O, ArSO$_2$—, ArSO—, ArS—, ArSO$_2$NH—, ArNH, (N—Ar)(N-alkyl)N-, ArC(O)—, ArC(O)NH—, ArNH—C(O)—, and (N—Ar)(N-alkyl)N—C(O)—, or together $R_1$ and $R_2$ comprise methylenedioxy; or 2. together with their ring carbons form a $C_{6-}$ or $C_{10-}$ aromatic fused ring system; or 3. together with their ring carbons form a $C^5-C_7$ fused cycloalkyl ring having up to two double bonds including the fused double bond of the -olium or -onium containing ring, which cycloalkyl ring is optionally substituted by one or more of the group consisting of alkyl, alkoxycarbonyl, amino, aminocarbonyl, carboxy, fluoro, or oxo substituents, or 4. together with their ring carbons form a 5- or 6-membered heteroaryl ring, wherein the 6-membered heteroaryl ring contains one to three atoms of N, and the 5-membered heteroaryl ring contains from one to three atoms of N or one atom of 0 or S and zero to two atoms of N, each heteroaryl ring is optionally substituted with one or more 1-pyrrolidinyl-, 4-[$C_6$ or $C_{10}$]arylpiperazin-1-yl, 4-[$C_6$ or $C_{10}$]arylpiperidin-1-yl, azetidin-1-yl, morpholin-4-yl, thiomorpholin-4-yl, piperidin-1-yl, halo or($C_1-C_3$)alkylenedioxy groups; or 5. together with their ring carbons form a five to eight membered heterocycle, wherein the heterocycle consists of ring atoms selected from the group consisting of carbon, nitrogen, and S(O)11, where n0, 1, or 2; and X is a biologically or pharmaceutically acceptable anion,
wherein aryl or Ar is optionally substituted with, in addition to any substitutions specifically noted, one or more substituents selected from the group consisting of acylamino, acyloxyalkyl, alkanoyl, alkanoylalkyl, alkenyl, alkoxy, alkoxycarbonyl, alkoxycarbonylalkyl, alkyl, alkylamino, $(C_1-C_3)$alkylenedioxy, alkylsulfonyl, alkylsulfinyl, ω-alkylenesulfonic acid, alkylthio, allyl, amino, ArC(O)-, ArC(O)NH-, ArO-, Ar-, Ar-alkyl-, carboxy, carboxyalkyl, cycloalkyl, dialkylamino, halo, trifluoromethyl, hydroxy, $(C_2-C_6)$hydroxyalkyl, mercapto, nitro, sulfamoyl, sulfonic acid, 1-pyrrolidinyl, 4-[$C_6$ or $C_{10}$]arylpiperazin-1-yl-, 4-[$C_6$ or $C_{10}$]arylpiperidin-1-yl, azetidin-1-yl, morpholin-4-yl, thiomorpholin-4-yl, and piperidin-1-yl; and
wherein heterocycles, except those of Ar, are optionally substituted with, in addition to any substitutions specifically noted, acylamino, alkanoyl, alkoxy, alkoxycarbonyl, alkoxycarbonylalkyl, alkyl, alkylamino, alkylsulfonyl, alkylsulfinyl, alkylthio, amino, ArC(O)-, ArO-, Ar-, carboxy, dialkylamino, fluoro, fluoroalkyl, difluoroalkyl, hydroxy, mercapto, sulfamoyl, or trifluoromthyl.

2. The compound of claim 1, wherein $R^2$ and $R^3$ are independently hydrogen, alkyl, or together form an alkylene bridge of 3–4 carbon atoms.

3. The compound of claim 1, wherein $R^1$ is hydrogen.

4. The compound of claim 1, wherein Z is an alkyl group of 1 to 7 carbon atoms.

5. The compound of claim 3, wherein Z is $C_1$ to $C_3$ alkyl.

6. The compound of claim 4, wherein $R^1$ is hydrogen.

7. The compound of claim 1, wherein Z is an alkyl group of 1 to 7 carbon atoms, arylcarbonyl, amino or alkoxycarbonylalkyl, or Z is according to the formula -CH($R^4$)(CN), or Z is -$CH_2$C(=O)$R^5$, where $R^5$ is a $C_6$–$C_{10}$ aryl group, said aryl group optionally substituted by one or more alkyl, alkoxy, halo, dialkylamino, hydroxy, nitro or $C_1$–$C_2$ alkylenedioxy groups.

8. The compound of claim 1, wherein Z is an alkyl group of 1 to 7 carbon atoms, arylcarbonyl, amino or alkoxycarbonylalkyl, or Z is according to the formula -CH($R^4$)(CN).

9. A compound of the formula:

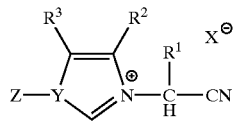

wherein:
Y is N;
Z is an alkyl group of 1 to 7 carbon atoms, arylcarbonyl, amino or (lower)alkoxycarbonyl(lower)alkyl, or Z is according to the formula -CH($R^4$)(CN), or Z is -$CH_2$C(=O)$R^5$, where $R^5$ is (a) a $C_6$–$C_{10}$ aryl group, said aryl group optionally substituted by one or more lower alkyl, lower alkoxy, halo, di(lower)alkylamino, hydroxy, nitro or $C_1$–$C_2$ alkylenedioxy groups or (b) heterocyclic group containing 4–10 ring members and 1–3 heteroatoms selected from the group consisting of oxygen, nitrogen and sulfur wherein the heterocyclic group is optionally substituted by one or more substituents selected from the group consisting of alkyl, oxo, alkoxycarbonylalkyl, aryl, and aralkyl group, and the one or more substituents are optionally substituted by one or more alkyl or alkoxy groups;
$R^1$ and $R^4$ are independently hydrogen, lower alkyl or phenyl optionally substituted with one or more halogen, lower alkyl, di(lower alkyl)amino or alkoxy groups;
$R^2$ and $R^3$ are independently hydrogen, lower alkyl, or together form an alkylene bridge of 3–4 carbon atoms; and
$X^-$ is a biologically or pharmaceutically acceptable anion.

10. A method of, in an animal, (i) improving the elasticity or reducing wrinkles of a skin, treating (ii) diabetes or treating, inhibiting the (iii) discoloration of teeth, or ameliorating one or more of the following conditions: (iv) adverse sequelae of diabetes, (v) kidney damage, (vi) damage to blood vasculature, (vii) hypertension, (viii) retinopathy, (ix) damage to lens proteins, (x) cataracts, (xi) peripheral neuropathy, (xii) osteoarthritis, or (xiii) damage to cardiovascular tissue due to heart failure, (xiv) improving myocardial elasticity, (xv) preventing damage to tissues in the intraperitoneal cavity caused by contact with elevated levels of reducing sugars, or (xvi) treating or ameliorating one of the conditions described above, the method comprising administering an effective amount of one or more compounds of the formula:

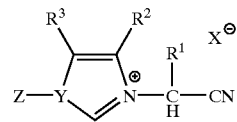

wherein
Y is N or
Z is absent when Y is S and, if present, Z is an alkyl group of 1 to 7 carbon atoms, vinyl, allyl, arylcarbonyl, amino or alkoxycarbonylalkyl, or Z is according to the formula -CH($R^4$)(CN), or Z is -$CH_2$C(=O)$R^5$, where $R^5$ is (a) a $C_6$–$C_{10}$ aryl group, said aryl group optionally substituted by one or more alkyl, alkoxy, halo, dialkylamino, hydroxy, nitro or $C_1$–$C_2$ alkylenedioxy groups or (b) heterocyclic group containing 4–10 ring members and 1–3 heteroatoms selected from the group consisting of oxygen, nitrogen and sulfur wherein the heterocyclic group is optionallysubstituted by one or more substituents selected from the group consisting of alkyl, oxo, alkoxycarbonylalkyl, aryl, and aralkyl group, and the one or more substituents are optionally substituted by one or more alkyl or alkoxy groups,
$R^1$ and $R^4$ are independently hydrogen, alkyl or phenyl optionally substituted with one or more halogen, alkyl, di(lower alkyl)amino or alkoxy groups; and
$R^2$ and $R^3$ are:
 1. independently selected from hydrogen, acylamino, acyloxyalkyl, alkanoyl, alkanoylalkyl, alkenyl, alkoxy, alkoxycarbonyl, alkoxycarbonylalkyl, alkyl, alkylarnino, $(C_1-C_3)$alkylenedioxy, allyl, amino, ωalkylenesulfonic acid, carbamoyl, carboxy, carboxyalkyl, cycloalkyl, dialkylamino, halo, hydroxy, $(C_2-C_6)$hydroxyalkyl, mercapto, nitro, sulfamoyl, sulfonic acid, alkylsulfonyl, alkylsulfinyl, alkylthio, trifluoromethyl, azetidin-1-yl, morpholin-4-yl, thiomorpholin-4-yl, piperidin-1-yl,4-[$C_6$ or $C_{10}$]arylpiperidin-1-yl, 4-[$C_6$ or $C_{10}$]arylpiperazin-1-yl, Ar {wherein, consistent with the rules of aromaticity, Ar is $C_6$ or $C_{10}$ aryl or a 5-or 6-membered heteroaryl ring, wherein 6-membered heteroaryl ring contains one to three atoms of N, and the 5-membered heteroaryl ring contains from one to three atoms of N or one atom of O or S and zero to two atoms of N, each heteroaryl ring is optionally fused to a benzene, pyridine, pyrimidine, pyridazine, pyrazine, or (1,2,3)triazine (wherein the ring fusion is at a carbon—carbon double bond of Ar)}, Ar-alkyl, Ar-O, ArSO$_2$-, ArSO-, ArS-, ArSO$_2$NH-, ArNH, (N-Ar)(N-alkyl)N-, ArC(O)-, ArC(O)NH-, ArNH-C(O)-, and (N-Ar)(N-alkyl)N-C(O)-, or together R$_1$ and R$_2$ comprise methylenedioxy; or 2. together with their ring carbons form a C$_6$-C$_{10}$- aromatic fused ring system; or 3. together with their ring carbons form a C$_5$–C$_7$ fused cycloalkyl ring having up to two double bonds including the fused double bond of the -olium or -onium containing ring, which cycloalkyl ring is optionally substituted by one or more of the group consisting of alkyl, alkoxycarbonyl, amino, aminocarbonyl, carboxy, fluoro, or oxo substituents; or 4. together with their ring carbons form a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each heteroaryl ring is optionally substituted with one or more 1-pyrrolidinyl-, 4-[C$_6$ or C$_{10}$]arylpiperazin-1-yl, 4-[C$_6$ or C$_{10}$]arylpiperidin-1-yl, azetidin-1yl, morpholin-4-yl, thiomorpholin-4-yl, piperidin-1-yl, halo or (C$_1$–C$_3$)alkylenedioxy groups; or 5. together with their ring carbons form a five to eight membered heterocycle, wherein the heterocycle consists of ring atoms selected from the group consisting of carbon, nitrogen, and S(O), where n=0, 1, or 2; and X is a biologically or pharmaceutically acceptable anion, wherein aryl or Ar is optionally substituted with, in addition to any substitutions specifically noted, one or more substituents selected from the group consisting of acylamino, acyloxyalkyl, alkanoyl, alkanoylalkyl, alkenyl, alkoxy, alkoxycarbonyl, alkoxycarbonylalkyl, alkyl, alkylamino, (C$_1$–C$_3$)alkylenedioxy, alkylsulfonyl, alkylsulfinyl, ω-alkylenesulfonic acid, alkylthio. allyl, amino, ArC(O)-, ArC(O)NH-, ArO-, Ar-, Ar-alkyl-, carboxy, carboxyalkyl, cycloalkyl, dialkylamino, halo, trifluoromethyl, hydroxy, (C$_2$–C$_6$)hydroxyalkyl, mercapto, nitro, sulfamoyl, sulfonic acid, 1-pyrrolidinyl, 4-[C$_6$ or C$_{10}$]arylpiperazin-1-yl-, 4-[C$_6$ or C$_{10}$]arylpiperidin-1-yl, azetidin-1-yl, morpholin-4-yl, thiomorpholin-4-yl, and piperidin-1-yl; and wherein heterocycles, except those of Ar, are optionally substituted with, in addition to any substitutions specifically noted, acylamino, alkanoyl, alkoxy, alkoxycarbonyl, alkoxycarbonylalkyl, alkyl, alkylamino, alkylsulfonyl, alkylsulfinyl, alkylthio, amino, ArC(O)-, ArO-, Ar-, carboxy, dialkylamino, fluoro, fluoroalkyl, difluoroalkyl, hydroxy, mercapto, sulfamoyl, or trifluoromethyl.

11. The method of claim 10, comprising administering an effective amount of one or more of the compounds wherein R$^1$ is hydrogen.

12. The method of claim 10, comprising administering an effective amount of one or more of the compounds wherein Z is an alkyl group of 1 to 7 carbon atoms.

13. The method of claim 10, comprising administering an effective amount of one or more of the compounds wherein Z is C$_1$ to C$_3$ alkyl.

14. The method of claim 12, comprising administering an effective amount of one or more of the compounds wherein R$^1$ is hydrogen.

15. The method of claim 10, comprising administering an effective amount of one or more of the compounds wherein Z is an alkyl group of 1 to 7 carbon atoms, arylcarbonyl, amino or alkoxycarbonylalkyl, or Z is according to the formula -CH(R$^4$)(CN), or Z is -CH$_2$C(=O)R$^5$, where R$^5$ is a C$_6$–C$_{10}$ aryl group, said aryl group optionally substituted by one or more alkyl, alkoxy, halo, dialkylamino, hydroxy, nitro or C$_1$–C$_2$ alkylenedioxy groups.

16. The method of claim 15, wherein Z is an alkyl group of 1 to 7 carbon atoms, arylcarbonyl, amino or alkoxycarbonylalkyl, or Z is according to the formula -CH(R$^4$)(CN).

17. The method of claim 10, comprising administering an effective amount of the one or more compounds to improve myocardial elasticity or reduce any loss of myocardial elasticity in heart failure.

18. A method of, in an animal, (i) improving the elasticity or reducing wrinkles of a skin, treating (ii) diabetes or treating, inhibiting the (iii) discoloration of teeth, or ameliorating one or more of the following conditions: (iv) adverse sequelae of diabetes, (v) kidney damage, (vi) damage to blood vasculature, (vii) hypertension, (viii) retinopathy, (ix) damage to lens proteins, (x) cataracts, (xi) peripheral neuropathy, (xii) osteoarthritis, or (xiii) damage to cardiovascular tissue due to heart failure, (xiv) improving myocardial elasticity, (xv) preventing damage to tissues in the intraperitoneal cavity caused by contact with elevated levels of reducing sugars. or (xvi) treating or ameliorating one of the conditions described above, the method comprising administering an effective amount of one or more compounds of the formula:

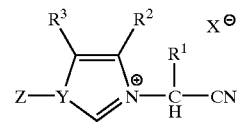

wherein:

Y is N or

Z is absent when Y is S and, if present, Z is an alkyl group of 1 to 7 carbon atoms, arylcarbonyl, amino or (lower) alkoxycarbonyl(lower)alkyl, or Z is according to the formula -CH(R$^4$)(CN), or Z is -CH$_2$C(0)R$^5$, where R$^5$ is (a) a C$_6$–C$_{10}$ aryl group, said aryl group optionally substituted by one or more lower alkyl, lower alkoxy, halo, di(lower)alkylamino, hydroxy, nitro or C$_1$–C$_2$ alkylenedioxy groups or (b) heterocyclic group containing 4–10 ring members and 1–3 heteroatoms selected from the group consisting of oxygen, nitrogen and sulfur wherein the heterocyclic group is optionally substituted by one or more substituents selected from the group consisting of alkyl, oxo, alkoxycarbonylalkyl, aryl, and aralkyl group, and the one or more substituents is optionally substituted by one or more alkyl or alkoxy groups, R$^1$ and R$^4$ are independently hydrogen, lower alkyl or phenyl optionally substituted with one or more halogen, lower alkyl, di(lower alkyl)amino or alkoxy groups;

R$^2$ and R$^3$ are independently hydrogen, lower alkyl, or together form an alkylene bridge of 3–4 carbon atoms; and X is a biologically or pharmaceutically acceptable anion.

19. A solid pharmaceutical dosage form comprising a therapeutically effective amount of one or more active compounds and a pharmaceutically acceptable excipient, the active compounds of the formula:

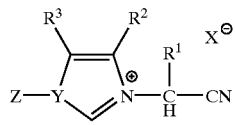

wherein:

Y is N or S;

Z is absent when Y is S and, if present, Z is an alkyl group of 1 to 7 carbon atoms, vinyl, allyl, arylcarbonyl, amino or alkoxycarbonylalkyl, or Z is according to the formula -CH($R^4$)(CN), or Z is -$CH_2$C(=O)$R^5$, where $R^5$ is (a) a $C_6$–$C_{10}$ aryl group, said aryl group optionally substituted by one or more alkyl, alkoxy, halo, dialkylamino, hydroxy, nitro or $C_1$–$C_2$ alkylenedioxy groups or (b) heterocyclic group containing 4–10 ring members and 1–3 heteroatoms selected from the group consisting of oxygen, nitrogen and sulfur wherein the heterocyclic group is optionallysubstituted by one or more substituents selected from the group consisting of alkyl, oxo, alkoxycarbonylalkyl, aryl, and aralkyl group, and the one or more substituents are optionally substituted by one or more alkyl or alkoxy groups, $R^1$ and $R^4$ are independently hydrogen, alkyl or phenyl optionally substituted with one or more halogen, alkyl, di(lower alkyl)amino or alkoxy groups; and $R^2$ and $R^3$ are:

1. independently selected from hydrogen, acylamino, acyloxyalkyl, alkanoyl, alkanoylalkyl, alkenyl, alkoxy, alkoxycarbonyl, alkoxycarbonylalkyl, alkyl, alkylamino, ($C_1$–$C_3$)alkylenedioxy, allyl, amino, ω-alkylenesulfonic acid, carbamoyl, carboxy, carboxyalkyl, cycloalkyl, dialkylamino, halo, hydroxy, ($C_2$–$C_6$)hydroxyalkyl, mercapto, nitro, sulfamoyl, sulfonic acid, alkylsulfonyl, alkylsulfinyl, alkylthio, trifluoromethyl, azetidin-1-yl, morpholin-4-yl, thiomorpholin-4-yl, piperidin-1-yl, 4-[$C_6$ or $C_{10}$]arylpiperidin-1-yl, 4-[$C_6$ or $C_{10}$]arylpiperazin-1-yl, Ar {wherein, consistent with the rules of aromaticity, Ar is $C_6$ or $C_{10}$ aryl or a 5- or 6-membered heteroaryl ring, wherein 6-membered heteroaryl ring contains one to three atoms of N, and the 5-membered heteroaryl ring contains from one to three atoms of N or one atom of O or S and zero to two atoms of N, each heteroaryl ring is optionally fused to a benzene, pyridine, pyrimidine, pyridazine, pyrazine, or (1,2,3)triazine (wherein the ring fusion is at a carbon—carbon double bond of Ar)}, Ar-alkyl, Ar-O, $ArSO_2$-, ArSO-, ArS-, $ArSO_2$NH-, ArNH, (N-Ar)(N-alkyl)N-, ArC(O)-, ArC(O)NH-, ArNH-C(O)-, and (N-Ar)(N-alkyl)N-C(O)-, or together $R_1$ and $R_2$ comprise methylenedioxy; or 2. together with their ring carbons form a $C_6$- or $C_{10}$-aromatic fused ring system; or 3. together with their ring carbons form a $C_5$–$C_7$ fused cycloalkyl ring having up to two double bonds including the fused double bond of the -olium or -onium containing ring, which cycloalkyl ring is optionally substituted by one or more of the group consisting of alkyl, alkoxycarbonyl, amino, aminocarbonyl, carboxy, fluoro, or oxo substituents; or 4. together with their ring carbons form a 5- or 6-membered heteroaryl ring, wherein the 6-membered heteroaryl ring contains one to three atoms of N, and the 5-membered heteroaryl ring contains from one to three atoms of N or one atom of O or S and zero to two atoms of N, each heteroaryl ring is optionally substituted with one or more 1-pyrrolidinyl-, 4-[$C_6$ or $C_{10}$]arylpiperazin-1-yl, 4-[$C_6$ or $C_{10}$]arylpiperidin-1-yl, azetidin-1-yl, morpholin-4-yl, thiomorpholin-4-yl, piperidin-1-yl, halo or ($C_1$–$C_3$)alkylenedioxy groups; or 5. together with their ring carbons form a five to eight membered heterocycle, wherein the heterocycle consists of ring atoms selected from the group consisting of carbon, nitrogen, and S(O)$_n$, where n=0, 1, or 2; and X is a biologically or pharmaceutically acceptable anion, wherein aryl or Ar is optionally substituted with, in addition to any substitutions specifically noted, one or more substituents selected from the group consisting of acylamino, acyloxyalkyl, alkanoyl, alkanoylalkyl, alkenyl, alkoxy, alkoxycarbonyl, alkoxycarbonylalkyl, alkyl, alkylamino, ($C_1$–$C_3$)alkylenedioxy, alkylsulfonyl, alkylsulfinyl, ω-alkylenesulfonic acid, alkylthio, allyl, amino, ArC(O)-, ArC(O)NH-, ArO-, Ar-, Ar-alkyl-, carboxy, carboxyalkyl, cycloalkyl, dialkylamino, halo, trifluoromethyl, hydroxy, ($C_2$–$C_6$)hydroxyalkyl, mercapto, nitro, sulfamoyl, sulfonic acid, 1-pyrrolidinyl, 4-[$C_6$ or $C_{10}$]arylpiperazin-1-yl-, 4-[$C_6$ or $C_{10}$]arylpiperidin-1-yl, azetidin-1-yl, morpholin-4-yl, thiomorpholin-4-yl, and piperidin-1-yl; and wherein heterocycles, except those of Ar, are optionally substituted with, in addition to any substitutions specifically noted, acylamino, alkanoyl, alkoxy, alkoxycarbonyl, alkoxycarbonylalkyl, alkyl, alkylamino, alkylsulfonyl, alkylsulfinyl, alkylthio, amino, ArC(O)-, ArO-, Ar-, carboxy, dialkylamino, fluoro, fluoroalkyl, difluoroalkyl, hydroxy, mercapto, sulfamoyl, or trifluoromethyl.

20. The solid pharmaceutical dosage form of claim 19 wherein the solid dosage form is a tablet, capsule or lozenge.

21. The solid pharmaceutical dosage form of claim 19, comprising a therapeutically effective amount of one or more of the compounds wherein R1 is hydrogen.

22. The solid pharmaceutical dosage form of claim 19, comprising a therapeutically effective amount of one or more compounds wherein Z is an alkyl group of 1 to 7 carbon atoms.

23. The solid pharmaceutical dosage form of claim 19, comprising a therapeutically effective amount of one or more compounds wherein Z is $C_1$ to $C_3$ alkyl.

* * * * *